United States Patent [19]

Chu et al.

[11] Patent Number: 5,489,274
[45] Date of Patent: Feb. 6, 1996

[54] ROTATABLE MEDICAL VALVE CLOSURE

[75] Inventors: Michael S. H. Chu, Brookline; Yem Chin, Burlington, both of Mass.; Andrew Cragg, Edina, Minn.; Barry N. Gellman, North Easton, Mass.

[73] Assignee: Boston Scientific Corporation, Watertown, Mass.

[21] Appl. No.: 211,650

[22] PCT Filed: Oct. 9, 1992

[86] PCT No.: PCT/US92/08687

§ 371 Date: Jul. 27, 1994

§ 102(e) Date: Jul. 27, 1994

[87] PCT Pub. No.: WO93/06877

PCT Pub. Date: Apr. 15, 1993

[51] Int. Cl.$^6$ .................. A61M 5/178; A61M 31/00; A61M 5/00
[52] U.S. Cl. .................. 604/167; 604/248; 604/169; 604/53
[58] Field of Search .................. 604/49, 51, 52, 604/53, 165, 167, 169, 248, 250, 256; 251/4–8

[56] References Cited

U.S. PATENT DOCUMENTS

| | | |
|---|---|---|
| 422,906 | 3/1890 | Booth . |
| 1,865,012 | 6/1932 | Jackson . |
| 2,458,027 | 1/1949 | Quist .................. 251/8 |
| 2,709,024 | 5/1955 | Lemoine et al. .................. 251/4 |
| 2,987,292 | 6/1961 | Teson et al. .................. 251/6 |
| 3,034,504 | 5/1962 | Winsor . |
| 3,197,173 | 7/1965 | Taubenheim . |
| 3,429,549 | 2/1969 | Swanson .................. 604/250 |
| 3,550,861 | 12/1970 | Teson .................. 251/6 |
| 3,585,996 | 6/1971 | Reynolds . |
| 3,805,830 | 4/1974 | Smith . |
| 3,813,077 | 5/1974 | Kolic . |
| 3,861,641 | 1/1975 | Kolic . |
| 3,920,215 | 11/1975 | Knauf .................. 251/7 |
| 4,016,879 | 4/1978 | Mellor . |
| 4,121,622 | 10/1978 | Forberg . |
| 4,243,034 | 1/1981 | Brandt . |
| 4,292,969 | 10/1981 | Raihle et al. .................. 251/4 |
| 4,314,555 | 2/1982 | Sagae . |
| 4,378,013 | 3/1983 | LeFevre .................. 251/7 |
| 4,417,576 | 11/1983 | Baran . |
| 4,423,725 | 1/1984 | Baran . |
| 4,464,171 | 8/1984 | Garwin . |
| 4,490,003 | 12/1984 | Robinson . |
| 4,496,348 | 1/1985 | Genese . |

(List continued on next page.)

FOREIGN PATENT DOCUMENTS 0745844  3/1956  United Kingdom .

OTHER PUBLICATIONS

Amplatz TractMaster System and Catheter–Medi–tech–Boston Scientific Corporation.
Torque Vise–Medi–Tech–Boston Scientific Corporation.
Tuohy–Borst Adapter with Side Port–Medi∝Tech–Boston Scientific Corporation.
FloSwitch HP–Medi–Tech–Boston Scientific Corporation.
Quality Check Valves from Burron∝Burron Medical Inc.

*Primary Examiner*—C. Fred Rosenbaum
*Assistant Examiner*—Frank Wilkens, III
*Attorney, Agent, or Firm*—Fish & Richardson

[57] ABSTRACT

An easy operating, durable closure device for controlling the closure of a passageway in for example valves and the like used in medical applications. The device includes a cam surface arranged about the circumference of a resilient tubing member. Rotation of the cam controls the radial position of a compression member that compresses the tubing member to effect closure. Such a closure device, or a two-part rotary closure device in general, is constructed to receive an accessory component such as a syringe, the rotary connecting movement of which automatically opens the closure device. The device may be used as a torqueable handle for a guidewire gripped in the passage. A large scale version of the device is joined to an introducer sheath, sized to pass an introducer catheter for e.g., a Green field filter, or to close upon a guidewire to prevent backflow of blood.

35 Claims, 13 Drawing Sheets

U.S. PATENT DOCUMENTS

| | | |
|---|---|---|
| 4,518,145 | 5/1985 | Keltz . |
| 4,540,411 | 9/1985 | Bodicky ................................. 251/4 |
| 4,570,898 | 2/1986 | Staubli ................................. 604/250 |
| 4,697,785 | 10/1987 | Tuseth . |
| 4,714,460 | 12/1987 | Calderon . |
| 4,813,938 | 3/1989 | Raulerson . |
| 4,883,461 | 11/1989 | Sawyer . |
| 4,917,668 | 4/1990 | Haindl . |
| 4,978,341 | 12/1990 | Niederhauser . |

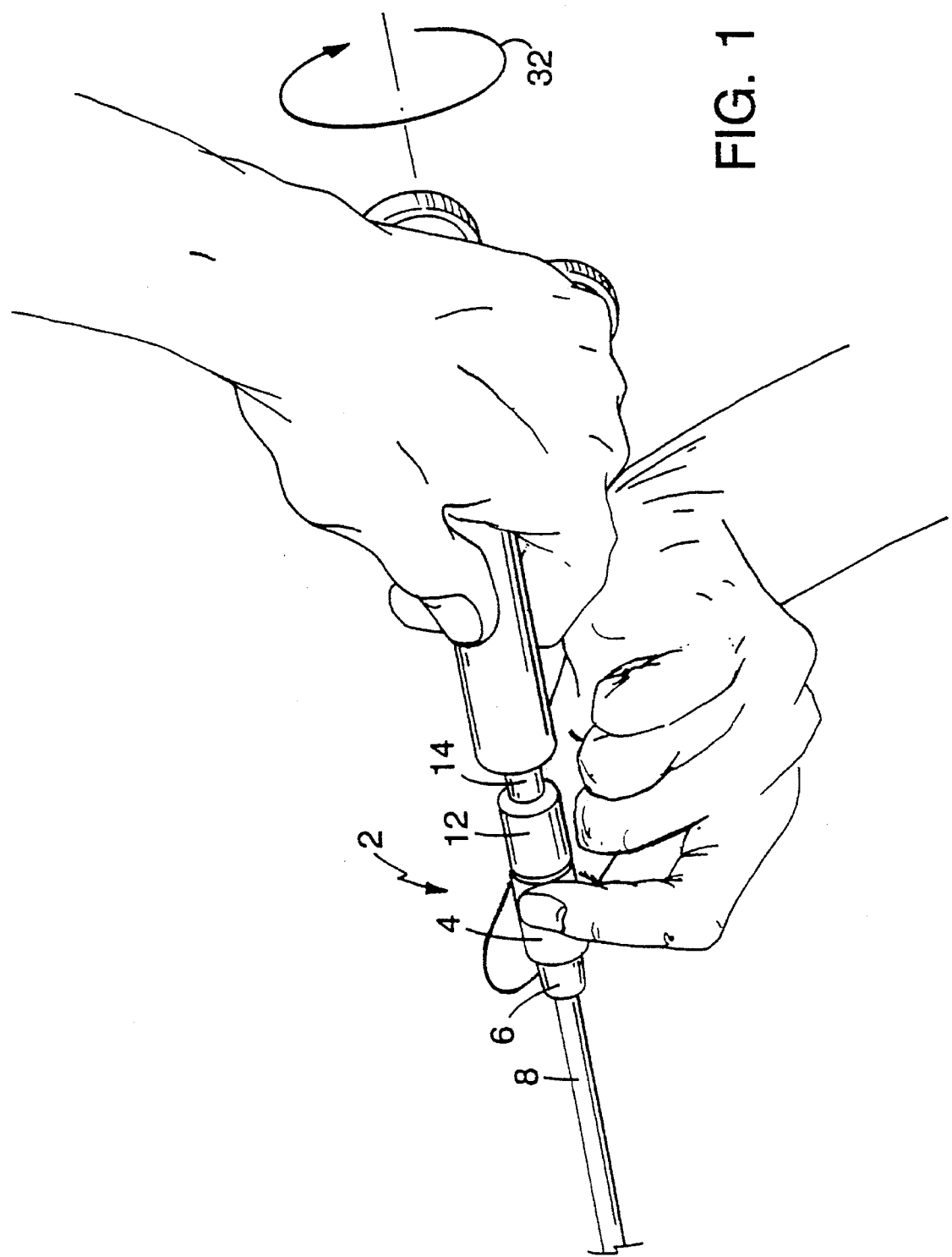

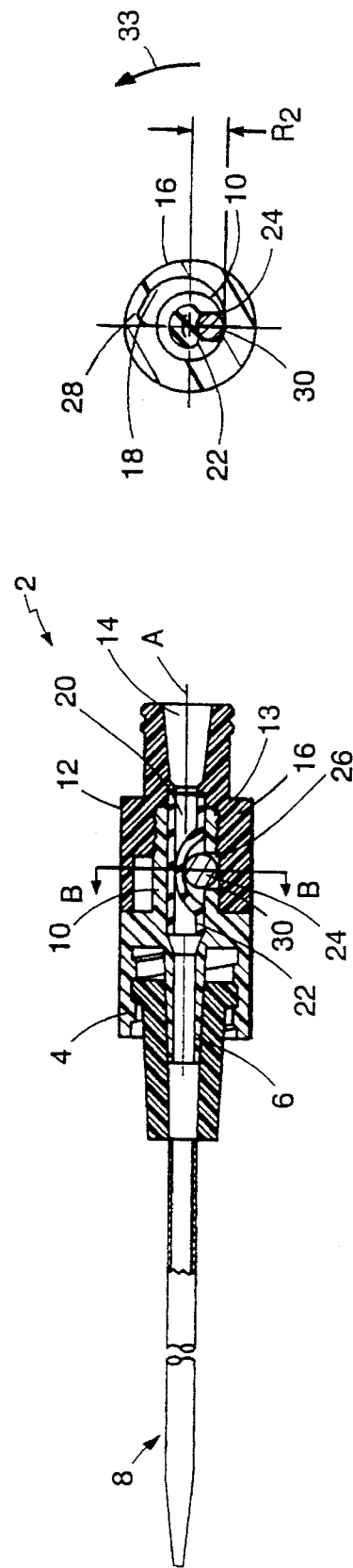
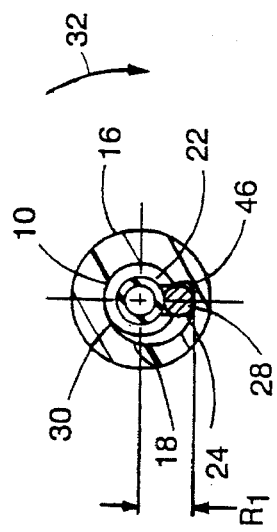
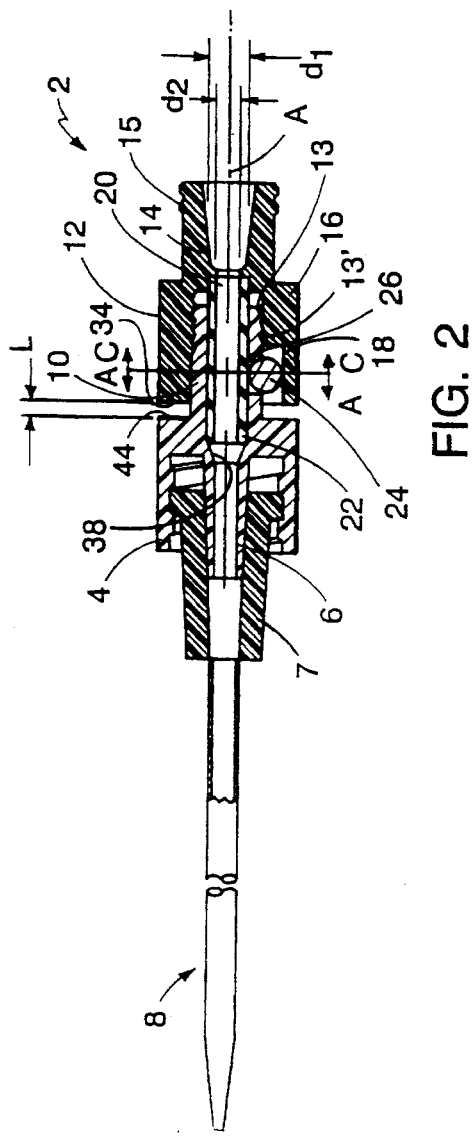

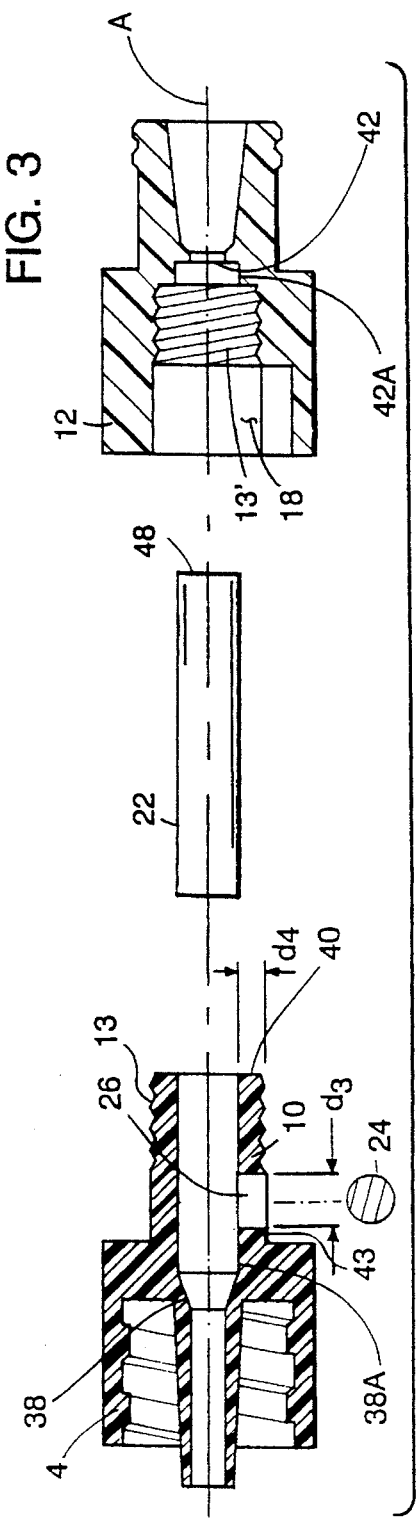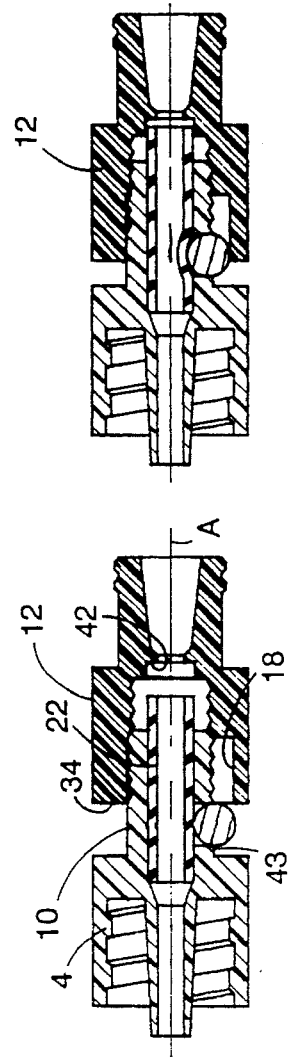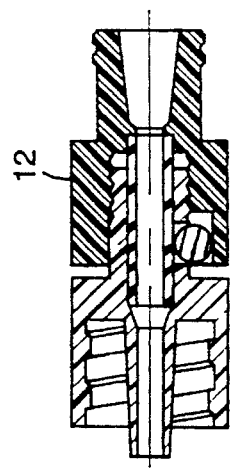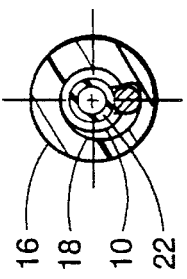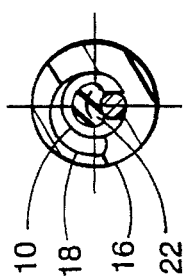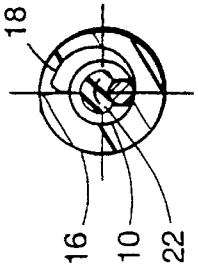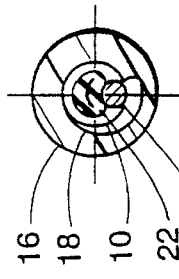

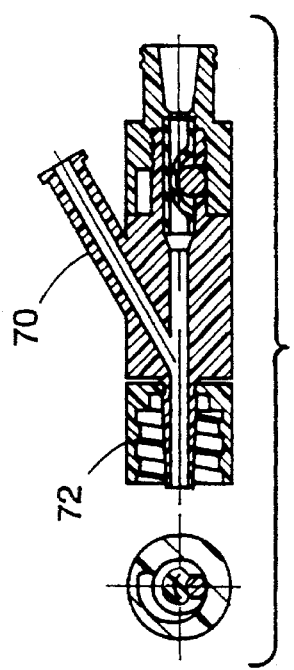
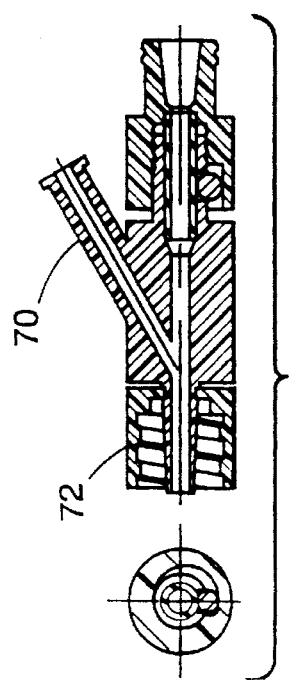
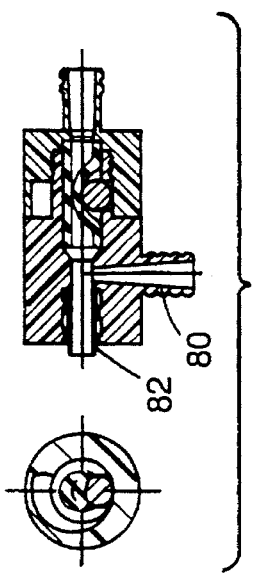
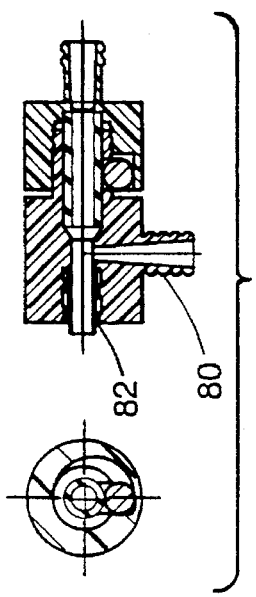
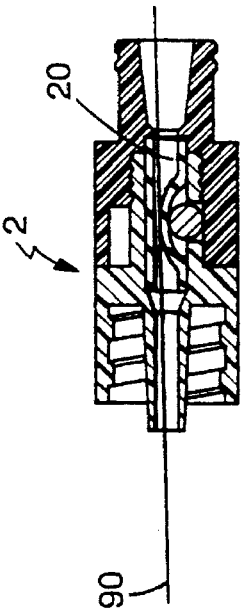
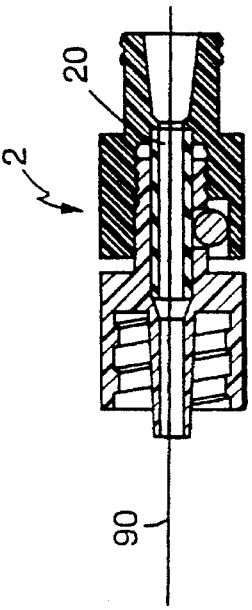

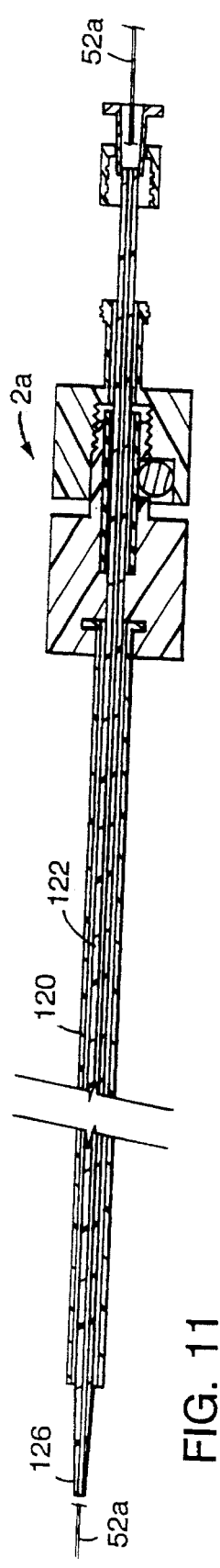
FIG. 11
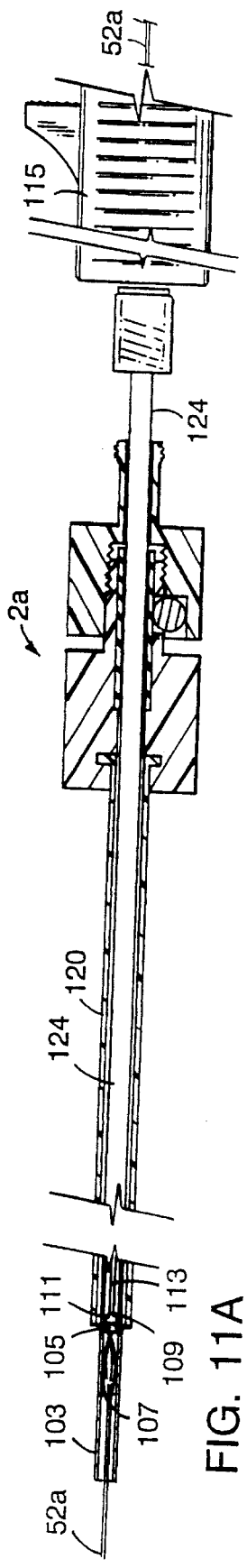
FIG. 11A
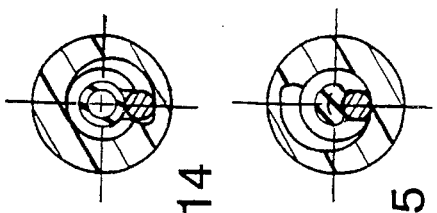
FIG. 14   FIG. 15
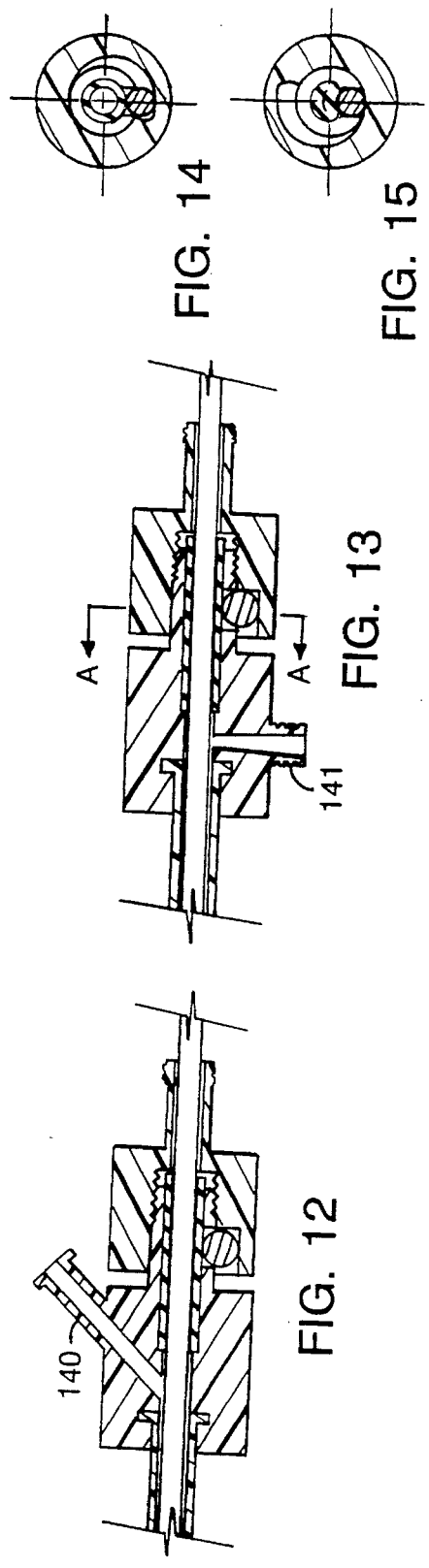
FIG. 13
FIG. 12

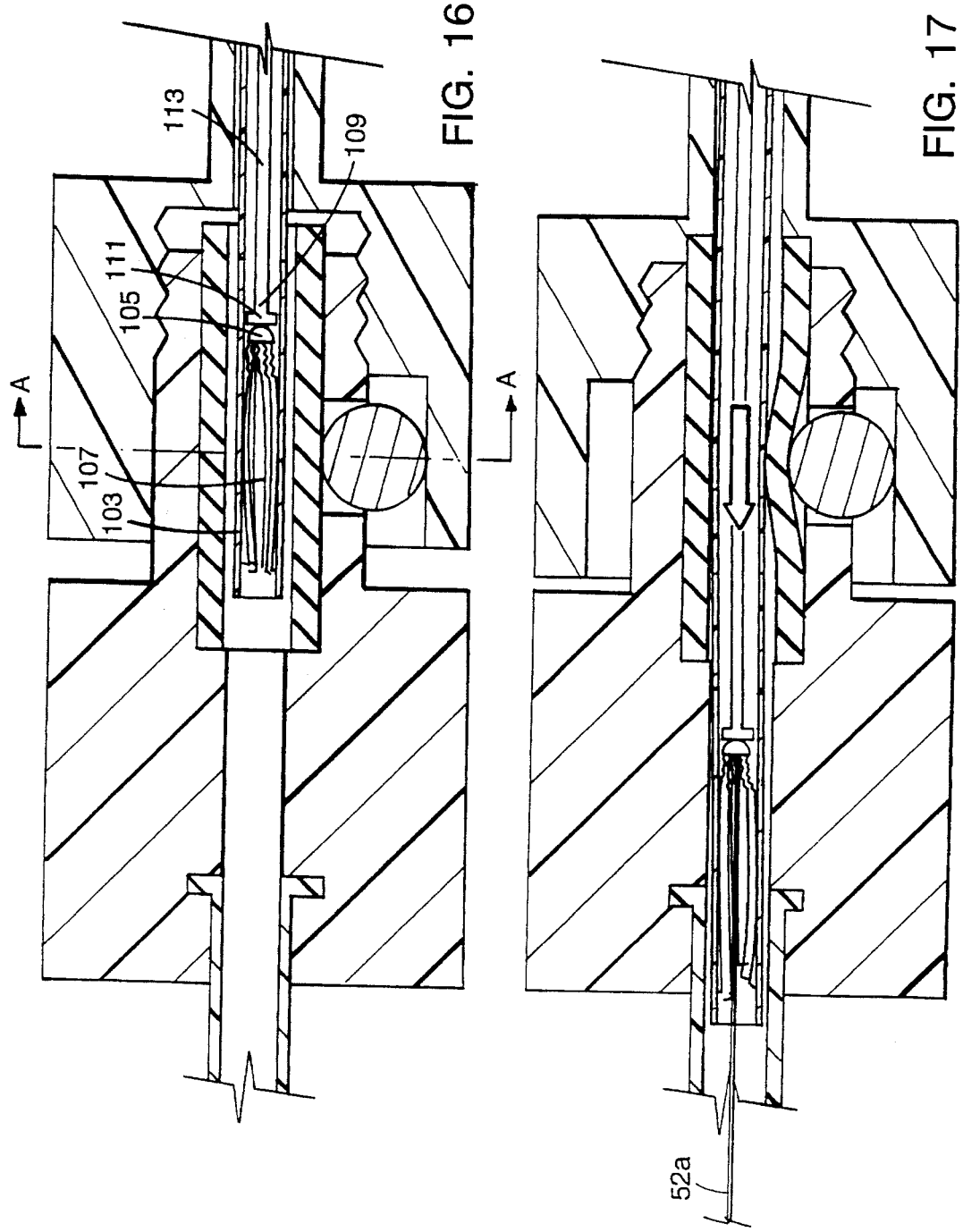

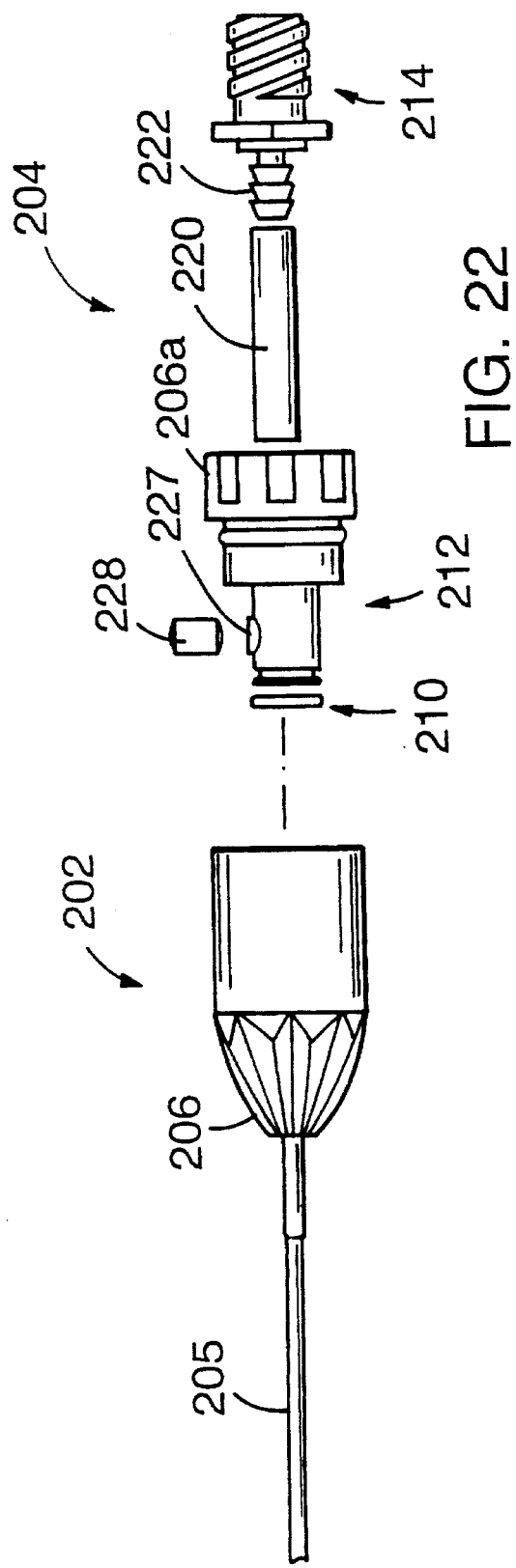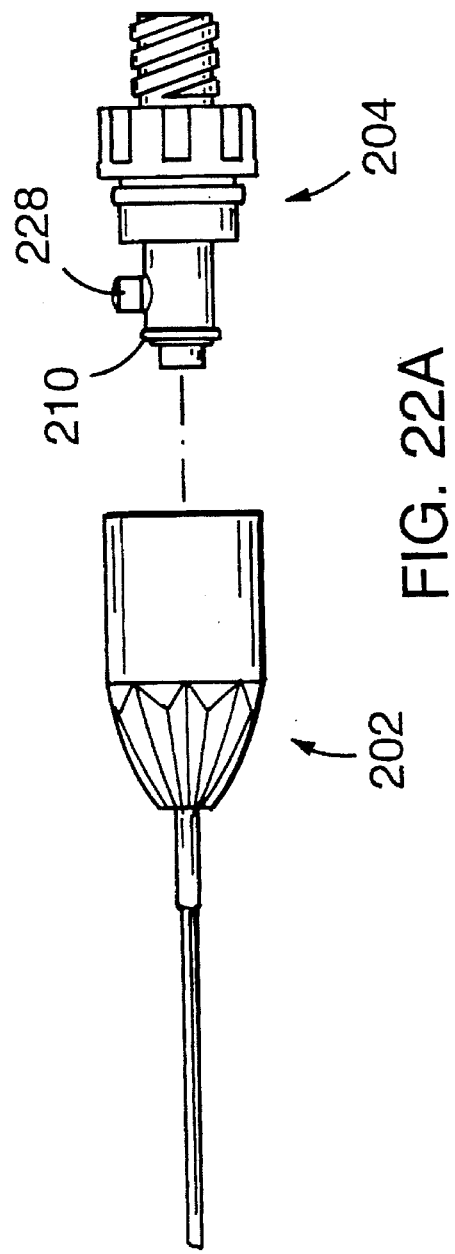
FIG. 22
FIG. 22A

ROTATABLE MEDICAL VALVE CLOSURE

FIELD OF THE INVENTION

This invention relates to through-channel valves and the like for medical applications, in particular, for the control of fluids and devices passing in or out of a patient's body. Operation of prior devices to some extent has been awkward and required more hand actions and the presence of more personnel than at times has been desirable.

BACKGROUND OF THE INVENTION

Catheters are placed inside blood vessels and body cavities, typically by being slid over guidewires. During placement, some way is needed to prevent backflow of blood or other fluid from the proximal end of the catheter. Many times it is also desirable, with minimum steps and effort, to attach a hand syringe to the proximal end of the catheter, open the catheter valve, inject fluids through the catheter and then remove the syringe and close the system. Many other applications require closure of a through-passage to, for example, control the flow of fluids as by a stopcock or to grip a device, such as a guidewire, to provide a handle to enable working the wire to achieve its insertion and accurate placement in the body.

While it is well known to use luer fittings for attachment of medical instruments, e.g. a syringe to a catheter, valves controlling flow that use luer fittings generally do not have through-passages and also, for the most part, require separate activating motions.

The attachment of an external instrument such as a syringe to the passageway of a closure device in a manner that also opens the closure device is also known, but in a form that has had significant limitations. Such a device, for example, is described in U.S. Pat. No. 4,243,034. The described device relies on an axial sliding motion for making the attachment and opening a valve by releasing one or more balls from depression into the wall of a resilient tube. This device is neither as simple nor as effective as desired by those in the field, and also fails to meet all needs for single-handed operation in flow-control devices.

Other known closure or wire-gripping devices provide partial benefits but fail to combine all desirable features in one unit. For example, one type of device, known as a Tuohy-Borst closure, comprises a cap which, when screwed on, axially compresses a captured thick-walled tubular segment (a grommet) to seal a passage through the tubular segment. This device is disadvantageous in that it requires many turns to seal the passage.

SUMMARY OF THE INVENTION

An object of the invention is to provide an improved device for closure of a through-passage for use, for example, as a valve for a catheter or as a gripping member for a device such as a guidewire placed in the through-passage or channel. Another object is to provide a closure device of a simple, rugged, inexpensive and durable construction that will not inadvertently disassemble by the activating motions. It is a further object to improve on the operation and configuration of closure devices for attachment and detachment to medical components, such as the attachment of a syringe to a catheter.

These objects are realized according to one aspect of the invention by a closure device based upon rotation of a rotary cam to displace a compression member against the side of a resilient tube. Such a closure device is, in one embodiment, constructed for both hand rotation and rotation by syringe, and the direction of rotation is the same for both attaching the syringe and opening a valve of the closure device.

These objects are further realized by a novel clamping or sealing device for clamping a guidewire or a catheter, operable in combination with an introducer sheath to prevent backflow of blood before or after insertion of the catheter or guidewire through the sheath; and by a kit comprising avena cava (e.g. Greenfield) filter, a stabilizer, a surrounding elongated placement catheter and an introducer sheath for insertion of the filter into the body.

The objects are further realized by a rotary valve that is opened by connecting motions of a syringe or the like, and closed by the reverse motion of disconnecting the syringe.

According to one principal aspect of the invention, a medical closure device is provided for controlling fluids or objects passing into or out of the body or the like, comprising in combination: a resilient member at least partially defining a through-passage having an axis; a body including first and second relatively rotatable body portions, the first body portion being stationary with respect to the resilient member and the second body portion including an internal cam having a cam surface oriented about and spaced from the axis of the passage with a first surface portion disposed relatively closer to the axis than a circumferentially spaced second surface portion; and a compression member positioned in a radially extending aperture in the first body portion and biased radially outward by the resilient member to maintain contact with the cam surface. The members of the combination are cooperatively related to enable adjustment of the radial compression of the resilient member for closing or opening the passage by relative rotation of the second body portion with respect to the first body portion to position, in dependent manner, the compression member radially closer to or further from the axis.

According to another principal aspect of the invention, a closure device is provided to which a cooperative component, such as a syringe, is attachable for communication therebetween comprising in combination: a resilient member at least partially defining a through-passage having an axis; a body portion constructed for attachably receiving the cooperative component by a rotatable connection, rotatable in a predetermined relative direction, the body portion being rotatable about the resilient member and including an internal cam having a cam surface oriented about, and spaced from, the axis of the passage. The cam has a first surface portion disposed relatively closer to the axis than a circumferentially spaced second surface portion, and a radially movable compression member disposed between and in contact with the cam surface and the exterior of the resilient member for adjusting the radial compression of the resilient member by rotating the body portion and positioning the compression member radially closer to or further from the axis. The body portion and the cam are arranged such that the direction of relative rotation for connection of the closure device to the component corresponds to the direction for effecting decreased compression of the resilient member by the compression member, the closure device being constructed to enable rotation motion in the direction that connects the component to the closure device to also open the through-passage, and the closure device also being constructed to enable reverse rotation motion in the direction that disconnects the component from the closure device to close the through-passage.

Preferred embodiments of this second aspect of the invention have one or more of the following features. The combination is constructed so that the rotational force required to rotate the body portion to effect change in the compression of the resilient member to open and close the passage is less than the rotational force needed, respectively, to complete the connection and disconnection of the cooperative component relative to the closure device. Preferably, the body portion is constructed to define a rotational luer lock fitting for interfitting with a matching fitting on the cooperative component. Also preferably, the rotatable body portion is threadably attached about the axis to a second relatively stationary body portion, the threads thereof being of opposite hand to threads of the rotatable connection between the closure device and the cooperative component, whereby rotation to connect together the cooperative components with the device causes the body portions to move apart. Preferably also, a stop surface is defined at the end of the second cam surface portion, arranged to engage the compression member and stop relative motion apart of the body portions when the compression member reaches passage-opening position, and the first and second body members are constructed to engage each other and stop threaded-together motion when the compression member reaches passage-closing position, the stops cooperating to enable positive connecting and disconnecting actions between the cooperative component and the closure device.

Further preferred embodiments of the second above-described aspect of the invention have one or more of the following features.

The device is constructed for use as a medical device in a flow path for fluid passing into or out of a living body wherein the proximal end of the device, relative to the living body, is constructed to be connected to a cooperative component in the form of a syringe or other injection device. Preferably, the distal end of the closure device relative to the living body is constructed to be connected to an angiographic catheter. Preferably also, the closure device further includes a side entry channel distal of the axial position of the compression member.

Preferred embodiments of either of the two principal aspects of the invention described above have one or more of the following features.

A stationary first body portion fixes the position of the tubing and a second body portion, carrying the cam surface, is mounted to rotate upon the first body portion. The tubing is preferably comprised of a silicone elastomer.

The first surface portion of the cam positions the compression member radially to completely close in fluid-tight manner the through-passage, and the second surface portion positions the compression member to fully open the through-passage for fluid flow.

The cam defines a smooth, spiral-form surface. Preferably, the compression member is a single ball-form member engaged upon the spiral surface. Also preferably the rotatable body portion is axially and rotatably positioned by a screw thread.

The rotatable body portion includes a first stop member which is engaged by the compression member preventing disassembly of the body portion by blocking further rotation. Preferably, the compression member is held axially fixed with respect to the tubing member, and the first stop member is a stop surface on the rotatable body portion at the end of the second portion of the cam surface for preventing rotation beyond the stop.

Also preferably, the rotatable body portion is positioned by a screw thread and the cam defines a spiral-form surface with an abrupt transition from the end of the second cam surface portion, furthest from the axis, to a portion of the body member closer to the axis, in a manner interacting with the compression member to permit continual rotation during assembly of the body portion in a screw-on direction in which the compression member is gradually, progressively compressed against the resilient member to the maximum at which state it remains until further rotation causes the second most furthest spaced portion of the cam surface to register with the compression member to permit a springing outwardly of the compression member to allow repetition of the rotational motion, whereas opposite rotation of the rotational body portion along the threads in screw-off direction is limited by the stopping of the compression member against the abrupt formation of the rotatable body portion.

Preferably also, a second stop member is provided for preventing rotation of the body portion beyond the first surface portion of the cam. Where the rotatable body portion is positioned by a screw thread, the first stop is preferably arranged adjacent to the second surface portion of the cam, furthest from the axis, upon which contact with the compression member is made to prevent further rotation in screw-off direction, and the second stop surface prevents rotation of the body in screw-on direction beyond the point at which the first surface portion of the cam, closest to the axis, is engaged with the compression member. Preferably, the second stop blocks further axial advance along the thread of the rotatable body portion. Preferably, the compression member is axially restrained in fixed position, relative to the resilient member, and a stationary body portion holds the resilient member in a fixed relation and defines a radially extending aperture in which the compression member is axially confined and is permitted to move radially against the resilient member.

Further preferred embodiments of each of the two principal aspects of the invention given above have one or more of the following features.

The tubing member is compressed axially and confined radially for sealing engagement of surfaces at its proximal and distal ends.

The body of the closure device and its through-passage are sized for passage therethrough of a guidewire providing, when the device is closed upon the guidewire, means for gripping and torquing the guidewire.

The body is attachable to tubing members for controlling the flow of fluid therethrough.

The rotatable body portion has an external surface exposed for engagement and rotatable operation by the hand of a user.

The closure device is constructed so that rotation of the rotatable body portion to open and close the through-passage is substantially one-half turn from stop to stop in opposite directions.

For control of a fluid at a pressure selected from over a wide pressure range, the thickness and character of the material of the resilient tubing member of the device is selected to withstand the selected pressure.

For control of a fluid at a flow rate selected from over a wide flow range, the inside diameter of the resilient tubing member is selected to accommodate the selected fluid flow rate.

The resilient tubing member and overlying body portion comprise clear plastic material enabling visual examination of flow through the through-passage.

The first and second body portions are formed of moldable material.

According to another broad aspect of the invention a closure device is provided to which a cooperative component is attachable for communication therebetween comprising in combination a two part body comprised of proximal and distal body portions, one portion of which is constructed for attachably receiving the cooperative component by a rotatable connection, rotatable in a predetermined relative direction, the parts of the body portion being relatively rotatable between an open position in which a passage is defined through the closure device and a closed position in with the passage is closed, the direction of relative rotation for connection of the closure device to the component corresponding to the opening direction of rotation of the body portion to which the component is connected, the closure device constructed to enable rotation motion in the direction that connects the component to the closure device to also open the passage, and to enable reverse rotation motion in the direction that disconnects the component from the closure device to close the passage.

In preferred embodiments the body portions, in open position define a through-passage through which a device can pass.

Also in preferred embodiment the wall defining said passage is constructed to close and seal or grip a device inserted into said through-passage.

Other objects, features and advantages of our invention will be apparent from the following detailed description of preferred embodiments of the invention taken together with the accompanying drawings wherein:

BRIEF DESCRIPTION OF DRAWINGS

FIG. 1 is a perspective illustration of a user holding the distal part of the closure device while connecting a syringe to the proximal part of the closure by turning.

FIG. 2 is a longitudinal cross-sectional view of the medical closure device of FIG. 1 in the open position, while FIG. 2A is a transverse cross-section of FIG. 2 along line A—A;

FIG. 2B is a longitudinal cross-sectional view of the closure device of FIG. 1 in the closed condition, while FIG. 2C is a transverse cross-section of FIG. 2B along line B—B;

FIG. 3 is an exploded view of the closure device of FIGS. 1 and 2;

FIGS. 4-4G illustrate steps in the assembly of the device, where FIGS. 4-4B are longitudinal cross-sectional views and FIGS. 4C-4G are a series of cross-sections, similar to FIG. 2A, taken through the center of the compression member at a sequence of rotary positions of the proximal body portion during assembly;

FIGS. 7 and 7A illustrate an alternative embodiment of the device with an angled side arm for access to the through-passage distal of the point of closure;

FIGS. 8 and 8A illustrate an alternative embodiment of the device with a 90 degree side arm entry for access to the through-passage;

FIGS. 9 and 9A illustrate use of the device as a gripping member with its attachment to a guidewire;

FIG. 11 is a view in longitudinal cross-section of a catheter introducer assembly comprising a closure device, attached introducer sheath and dilator within the sheath;

FIG. 11A is a view similar to FIG. 10 of the introducer sheath of FIG. 11 through which a placement catheter containing a vena cava filter and stabilizer assembly extends;

FIG. 12 illustrates in longitudinal cross-section the device of FIG. 11 modified to have an angled side arm access port connected to the through-channel distal of the point of closure;

FIG. 13 illustrates in longitudinal cross-section the device of FIG. 11 modified to have a 90 degree side arm access port connected to the through-channel distal of the point of closure;

FIGS. 14 and 15 show in cross-section along line A—A of FIG. 13 relative positions of the compression member and the resilient tubing in open and closed positions, respectively;

FIGS. 16-17 show in cross-section the device of FIG. 11 with details of the vena cava filter and stabilizer within the placement catheter as they are inserted through the closure device and introducer sheath;

FIG. 18 shows in cross-section along line A—A of FIG. 16 the positions of the cam and other components in clamping and sealing relationship upon a guide wire while

FIG. 22 shows a reduced exploded view of the device of FIG. 21.

FIG. 22A shows a partially assembled view of the device of FIG. 21.

DETAILED DESCRIPTION OF THE PREFERRED EMBODIMENTS

Structure

Figure 5:
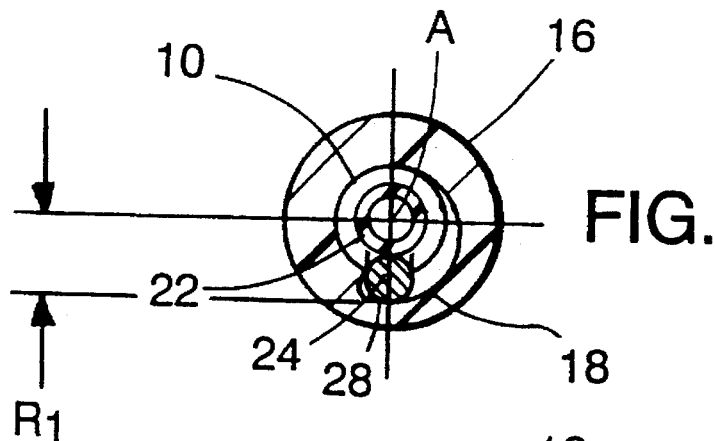
FIGS. 5-5C taken in the direction of Line C—C in FIG. 2 illustrate gradual closure of the through-passage during operation showing positions of the cam surface and the radially moveable compression member.
Figure 5A:
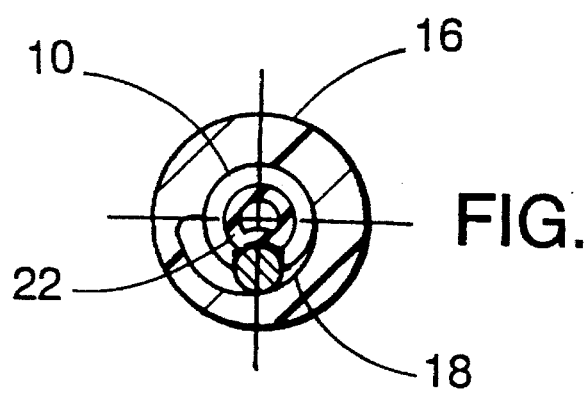
Figure 5B:
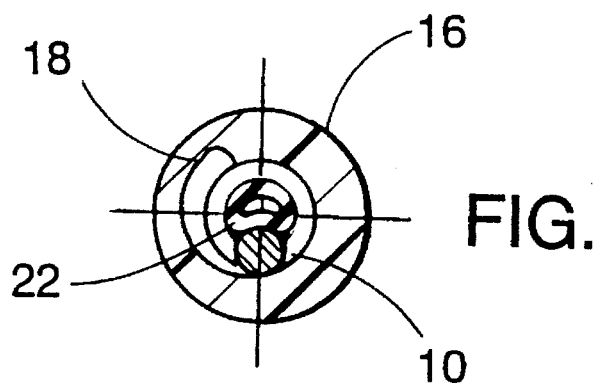

Referring to FIGS. 1 to 3, medical closure device 2 includes a distal body member 4 having a distal end 6 configured as a male luer locking member for attachment, for example, to the hub 7 of an angiographic catheter 8 (5 French), and a proximal end 10 which is threadably (threads 13) attached to a proximal body member 12. The proximal body member includes a proximal end 14 which is adapted as a threaded (threads 15) female locking luer attachment and a distal end 16 that includes threads 13'. Overall length of this embodiment is about 3 cm and diameter about ½ inch as described below.

The external cylindrical surface of the body member provides a convenient gripping surface for hand operation of the closure device.

The distal end of the proximal body includes in its interior an inner cam 18 having a cam surface that is circumferentially arranged about axis A of the device. Channel 20, having an axis A, extends through the device (FIG. 2). A tubing member 22, preferably silicone tubing, is positioned in the channel. In this preferred embodiment, the silicone tubing has, in unstressed condition, an outside diameter $d_1$ of approximately 0.150 inch, an inside diameter $d_2$ of 0.060 inch, and a wall thickness of about 0.045 inch. When installed in the body member 38A and taper 42A, the tubing is compressed and supported by the walls of the body so that it, in open condition, has an outside diameter of 0.141 inch and an internal diameter of 0.055 inch.

A valve is formed by a spherical compression member 24, preferably a stainless steel ball with a diameter of about 0.125 inch, which is biased radially outward by tubing member 22 such that the compression member maintains contact with cam 18. As illustrated particularly in FIG. 3, compression member 24 is positioned in an aperture 26 in the proximal portion 10 of distal body 4 to prevent axial motion of the compression member, but permit and guide its radial movement. Preferably, the aperture has a diameter $d_3$ of 0.128 inch, and a depth $d_4$ of 0.056 inch.

To effect opening of the through-passage, the relative rotation of distal body 4 and proximal body 12 in direction 32 is adjusted such that the compression member is positioned along portion 28 of cam surface 18, furthest in radial position, distance $R_1$, from axis A, as illustrated in FIGS. 2 and 2A. The cross-sectional views of FIGS. 2A and 2C illustrate that when rotated clockwise from the closed position (FIG. 2C), the movement of the proximal body member causes the compression member to disengage its compression of the tubing in a linear fashion by action of the cam surface, until a point is reached when the compression member no longer compresses the tubing and is positioned on cam surface portion 28. The compression member then comes into abutment with butt stop 46 (FIG. 2A) formed by the proximal body, preventing further rotation.

Similarly, to effect closure of the through-passage, proximal body member 12 is rotated counter-clockwise relative to distal body member 4 (arrow 33 on FIG. 2C) causing compression member 24 to be positioned on portion 30 of the cam which is closest, dimension $R_2$, to axis A of the through-passage. This moves the compression member radially inward to compress the tubing member 22 and reduce and close the opening of the through-passage, as illustrated in FIGS. 2B and 2C.

Left-handed threading 13 and 13' is used in joining the distal and proximal body portions. Therefore, as proximal body member 12 is rotated in a counterclockwise direction, as viewed from the proximal end of the closure device (in the "screw-on" direction, indicated by arrow 33), the proximal body member moves axially dietally, i.e., closer to distal body member 4. The cam is oriented such that full closure of the free passage is reached at a point of the counterclockwise rotation when surfaces 34 and 44 of the proximal and distal body-members, respectively, butt with one another, giving the feel also of a definite stop point for the fully closed position.

Thus, in this embodiment, in which the closure device is used as a stop cock with a syringe attachment, the cam is oriented such that opening of the through-passage is effected by clockwise rotation and closure of the through-passage is effected by counter-clockwise rotation of the proximal body member, as viewed from the proximal end of the device. This arrangement advantageously allows the user to attach the syringe and open the passage, or close the passage and remove the syringe, with a single motion.

The axial travel of the proximal body member between the fully open and fully closed positions (FIGS. 2A and 2C) is indicated by gap "L" (FIG. 2). In the preferred embodiment, this distance is about 0.030 inch and is covered by an approximate 180° rotation of the proximal body member. During rotation, the portion of the cam surface contacting the ball-form compression member lies at a radial distance from the axis A that changes by a similar dimension, 0.030 inch between open and closed positions.

Luer connector 14 (with Luer taper from dimension $d_1$ to $d_2$ and external Luer threads) is configured in the common manner, to require a clockwise rotation of an external component, such as a syringe, for attachment to the closure device 2. With this rotation arrangement and the closure device in the closed condition initially, the proximal body member resists relative rotation when the syringe is being attached because the tubing member under compression by the compression member produces frictional drag. The syringe thereby can be initially lead on to the luer thread. The resistance of the cam arrangement is overcome when the component becomes partially engaged on luer connector 14 by the clockwise rotation and resistance of the luer connection increases as normally occurs. At that point, further clockwise rotation of the syringe causes simultaneous clockwise rotation of the proximal body portion, and channel 20 is opened as the compression member moves along cam surface to cam portion 28. When the compression member reaches the butt stop 46, the proximal body portion is stopped from rotation, and further clockwise rotation of the syringe enables the luer connection to reach its final locked position.

When, after use, the syringe is to be removed, the syringe is subsequently rotated in the counter-clockwise direction. The proximal body portion 12 rotates simultaneously with the syringe, because of the locking friction of the luer in its locked position, (there is also less resistance exerted on cam surface 18 by compression member 24 when the tubing, in open position, is not significantly compressed). After the proximal body portion has been rotated such that compression member 24 is moved into contact with cam portion 30 and the through-passage is closed, surfaces 44 and 34 of the two body members move into abutment by the left-handed mounting threads, establishing a definite stop point indicative of the closed condition of the through-passage. The syringe is then disconnected by its further rotation in the same direction to overcome the resistance of the luer lock.

In an embodiment where the closure device is used with a syringe as a connected component, the device preferably has an outside diameter of about 0.445 inch and is approximately 3 cm. in length. A typical syringe may have an outside diameter of 0.75 inch and length of 10 cm. A particular advantage of the preferred embodiment incorporating the described rotary cam/ball valving arrangement described is its dual operability, i.e., its ability to be opened or closed either by hand or by attachment of an external component such as a syringe.

Another particular advantage is that, once assembled, the simple construction of the device prevents its disassembly. Clockwise rotation of the proximal body member 12 causes the cam surface to ride along the compression member to effect opening of the through-passage. When the relative rotation of the distal and proximal body members places portion 28 of the cam surface in contact with compression member 24, further rotation is prevented by butt surface 46 which engages the axially-stationary compression member. This prevents further clockwise rotation and any disassembly of the device in this direction.

Similarly and conversely, when the relative rotation is such that the compression member 24 or ball is adjacent to cam surface portion 30 closest to axis A, end 34 of the proximal body member engages surface 44 of the distal body member, thereby preventing any further rotation and possible damage to the compression member or body members.

With rotation being thus limited in either direction, disassembly of the device by rotation of threads 13 and 13' is entirely prevented.

This feature of having a device of few and rugged parts that is incapable of being disassembled is of particular importance since it makes the device virtually fail-safe because it can neither be overtightened nor disassembled which could lead to loss of parts, introduction of dust, blood, etc.

Preferably, markings are on the body of the closure device so that the operator can tell whether the device is in the ON or OFF position and know the direction for rotation to the other setting.

Referring to FIG. 3 as well as FIGS. 4 to 4G, assembly of an embodiment of the device is illustrated.

Assembly of the distal body member with the proximal body member involves an interference fit of the elastomeric tube with the two slightly tapered female connections, one on the proximal end of the distal body member 38A and one on the distal end of the proximal body member 42A. The significant taper 38 of channel 20 serves to accomodate the thickness of the tube, to prevent tube movement while allowing for variation in the length of the tube, and to facilitate insertion of a guidewire or catheter through the channel. The taper of the ends of the channel in each body portion which the tube ends enter for their interference fit are tapered only slightly for achieving the desired interference. The tubing is first inserted into the channel of one member using a drop of silicone oil on the tube during assembly. This facilitates the joinder while also assisting in the combined radial and axial compression sealing of the tubing within the channel. Although oil is not needed on the compression member and in the recess within which it operates, some of the oil from the tubing may come into contact with the compression member which presents no problem and can benefit smooth operation of the closure device.

The tubing, due to the surrounding support provided by the housing walls that define channel 20, is capable of withstanding fluid pressures of greater than 1000 psi. Thus the device may be used for example, to handle pressures of 300–400 psi where a contrast media is to be injected rapidly from a syringe, and pressures up to 1,050 psi when used with a contrast media injector. High injection pressure is required in such an application so that the contrast media is rapidly totally injected and thus it is not dispersed. The pressure is needed to overcome the flow resistance of the relatively long path it must travel to reach the point in the body for the intended fluoroscopic medical observation.

In assembly, proximal body 12 is aligned with, and partially threaded onto, the proximal portion 10 of distal body 4 such that end 34 is roughly in alignment with the edge of aperture 26 in which the compression member is placed (FIG. 4). Tubing member 22 has at this point already been positioned in the distal body member 4. The length of tubing member 22 (overall length about 0.480 inch) extends from a taper 38 in distal body 4 to beyond (about 3.0 mm) the most proximal end 40 of the distal body member 4, so that when assembly is complete, the proximal end of tube 48 reaches surface 42 to position the tube, though the main scaling effect is achieved by interference with the taper of the associated body portion into which the proximal end of the tube fits. Use of the resilient tubing in this manner produces both a fluid-tight and an air-tight seal, and allows operation with the high fluid pressures mentioned.

In the next step of assembly,-compression member 24, here in the form of a ball, is positioned in aperture 26 (FIG. 4). The compression member's diameter is larger than depth $d_4$ of the aperture on the proximal portion of the distal body member, so the compression member will naturally extend beyond the outer edge 43 of proximal body portion 10 of distal body 4, being biased outwardly by the resilient tubing member 22 (FIG. 4). The compression member also extends beyond cam surface 18, even with the cam surface rotated to a position radially furthest from axis A, i.e. in open position.

To proceed with assembly, the compression member is then depressed radially, for example with the finger, so that it does not extend beyond surface 18 and, simultaneously, proximal body portion 12 is rotated in the "screw-on" direction counter-clockwise a number of turns such that its distal end overlaps the compression member (FIG. 4A). Whereas the rotatable body portion defines a spiral-form cam surface with an abrupt transition from the end of the cam surface portion 28, furthest from the axis, to a portion of the body member closest to the axis, continual rotation during assembly of the body portion in screw-on direction is permitted by the parts. The compression member is gradually progressively compressed against the resilient member until the maximum is reached at which state it remains until sufficient further rotation causes the abrupt transition and surface portion 28 of the cam surface to register with the compression member, (FIG. 4B) and permit spring outwardly of the compression member to permit repetition of the rotational motion, (whereas opposite rotation of the rotatable body portion along the threads is limited by stopping of the compression member against the abrupt formation, butt surface 46, of the rotatable body portion). FIGS. 4C through 4G show various positions of the cam surface relative to the compression member during the assembly stages. As discussed, because of stop surfaces 34, 44, 46 (FIGS. 2 and 2A), the device, once assembled, cannot be disassembled by rotation in either direction.

Figure 5C:
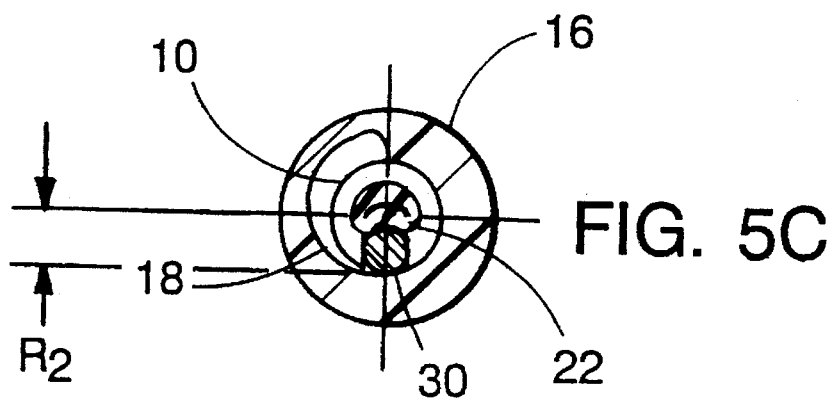

Continuous gradual control of the size of the through-passage is illustrated in the series of FIGS. 5 to 5C, which show, in cross-section taken along line C—C of FIG. 2, cam surface 18, compression member 24, conformable tubing member 22 and axis A. As illustrated, the distance from cam surface 18 to axis A varies continuously along a spiral path of the cam from a maximum distance $R_1$ (about 0.177 inch) near end 28 (FIG. 5) to a minimum distance $R_2$ (about 0.107 inch) at end 30 (FIG. 5C).

The conformable interior of the resilient tubing provides a seal about an object, such as a guidewire, if present in the through-passage when the device is in the closed position.

Further, in the embodiment described in the figures above, the use of a freely rotating spherical compression member or ball allows for through-passage opening adjustments by slight rotation in either direction.

Figure 6:
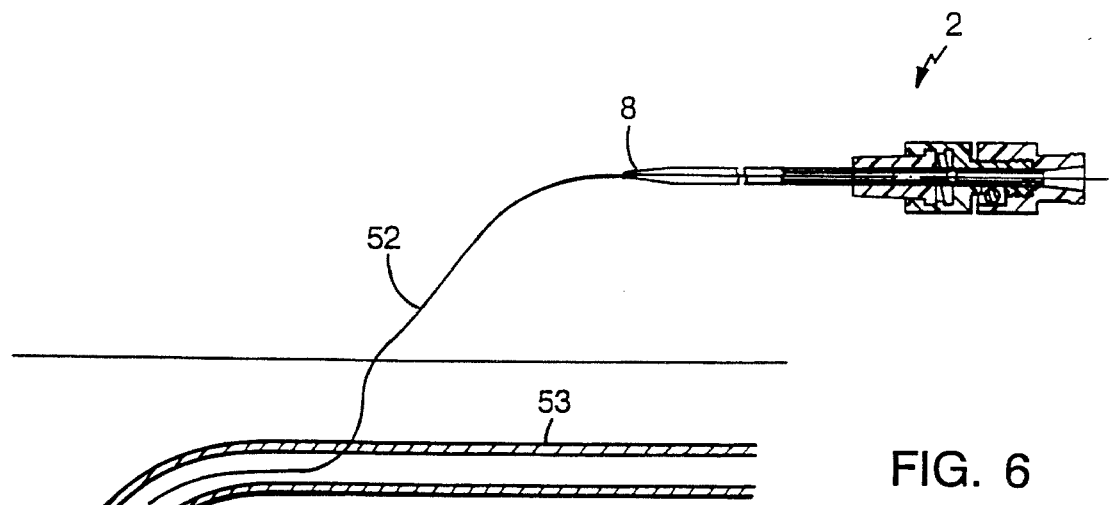
FIGS. 6 to 6E illustrate use of the device in a catheterization operation.
Figure 6A:
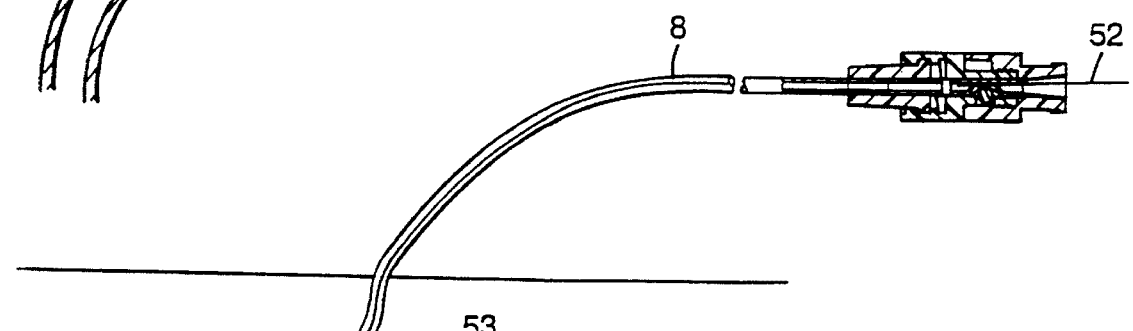
Figure 6B:
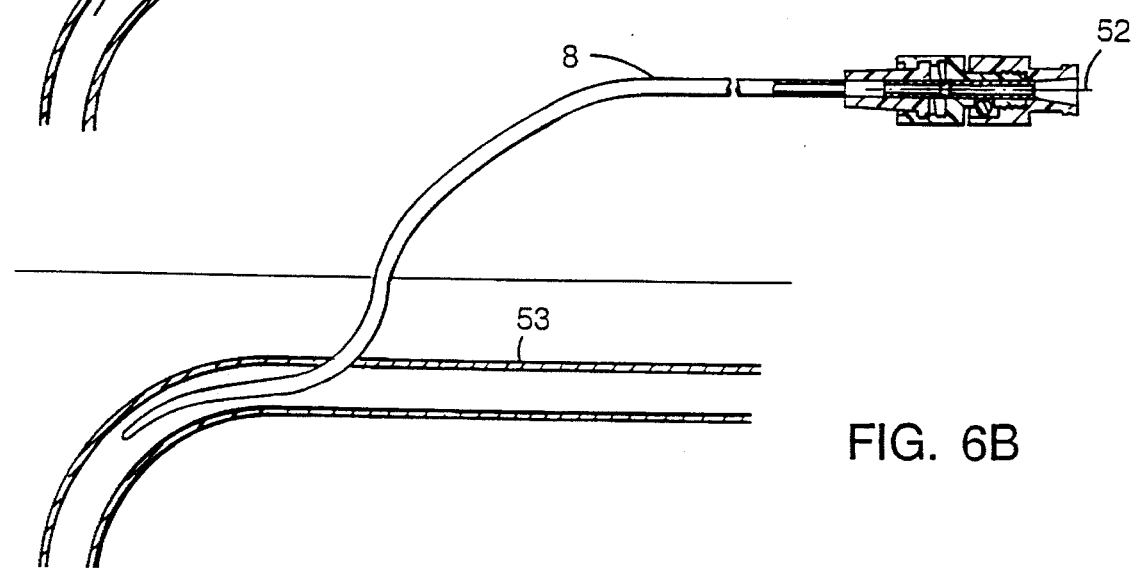
Figure 6C:
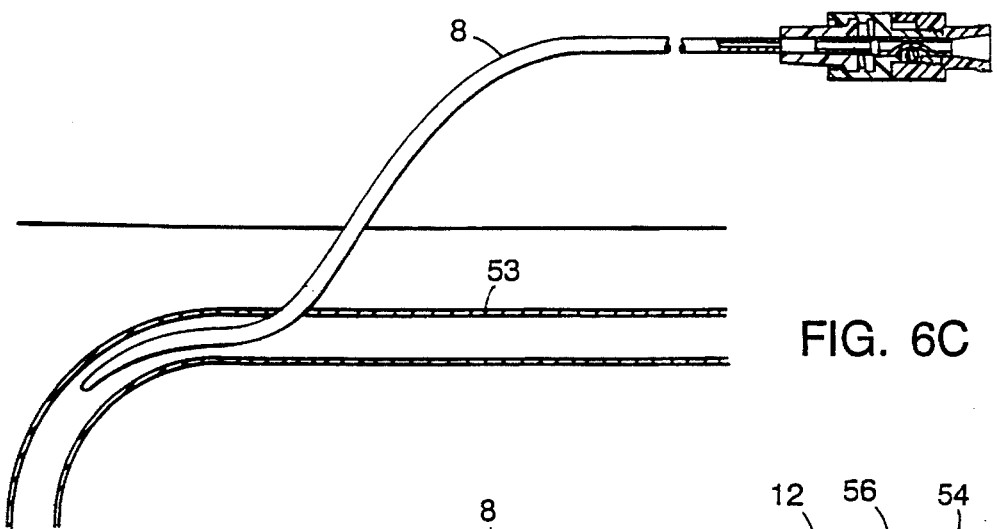

One particular use of the closure device is in the medical field for providing through-channel access to a catheter, such as an anglographic catheter. Referring to FIG. 6, in a typical catheterization operation such as an angiographic procedure, a guidewire 52 is positioned at the location of a desired arterial passageway (FIG. 6), such as the femoral artery for example, using an introducer needle (not shown) applying the Seldinger technique. An anglographic catheter 8 having attached thereto the closure device 2, is threaded over the guidewire 52 such that the catheter is positioned in the artery 53 (FIG. 6A). For this operation the closure device is in the open position, or alternatively, in a partially opened position to minimize backflow of blood alongside of the exterior of the catheter from the artery. The guidewire and catheter may be further positioned within the artery by manually rotating the proximal body member to the closed position, while gripping the guidewire 52 (FIG. 6A). The guidewire, catheter and device can thus be moved and torqued as a single unit to aid positioning as well as avoid punctures and other disturbances of the vessel (arterial passageway). With the catheter properly positioned, the device may be placed in the open position, again by manual rotation, to open the through-passage and allow removal of the guidewire (FIG. 6B). After removal of the guidewire, the valve is manually closed (FIG. 6C).

Figure 6D:
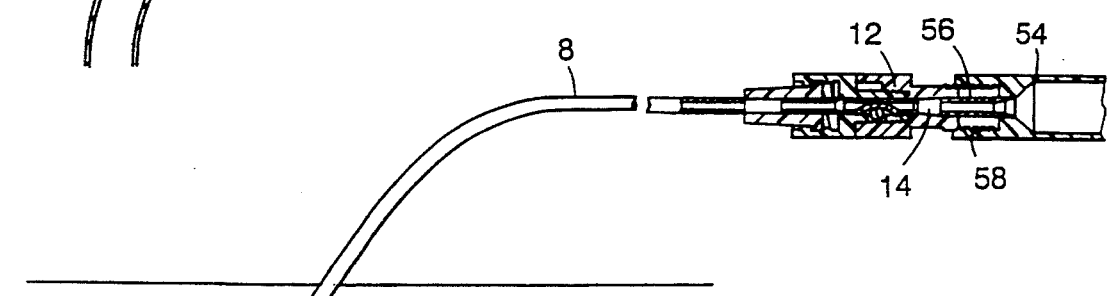
Figure 6E:
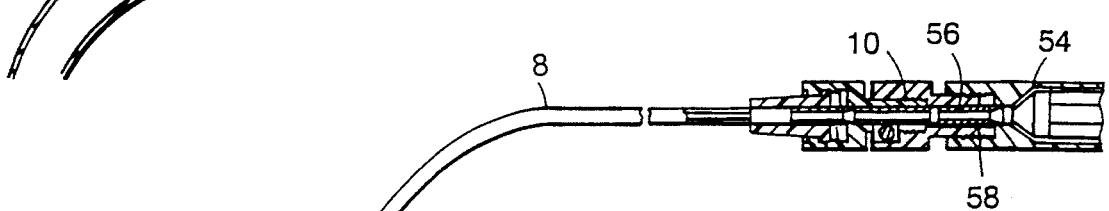

In the embodiment of FIGS. 6 through 6E, the closure device can have the catheter permanently attached, as by insert molding, or removably attached as by matching luer connectors, to the distal end of the distal body member.

During the catheterization procedure, it is often desirable to inject fluids, such as contrast fluids for radiographic imaging, through the catheter. To effect injection, a syringe 54 with a distal end 56 adapted as a male luer lock fitting having locking thread 58 (end thread) is connected to the female luer adaptor 14 defined at the proximal end of the proximal body portion 12 by clockwise, "screw-on" rotation of syringe 54. The syringe rotates relative to the proximal end 12 before reaching a pre-engagement position (FIG. 6D). After reaching this position, at which point locking thread 58 is initially engaged, further rotation of the syringe causes simultaneous rotation of proximal body member 12 thereby automatically effecting opening of the through-passage (FIG. 6E). When the compression ball reaches the end of the cam surface and engages butt surface 46, rotation of the distal body portion is stopped and further rotation of the syringe seats the luer lock. Injection of fluid can then be commenced. After injection, rotation of the syringe in the opposite, counter-clockwise direction causes simultaneous rotation of proximal body member 12 of the device, thereby automatically closing the through-passage. After the through-passage is completely closed, further rotation of the proximal portion is prevented by butting of the body portions together, as discussed above, and the syringe may then overcome the resistance of the luer lock and rotate relative to the proximal portion and be unlocked and removed.

Referring to FIGS. 7 and 7a, another embodiment of the device is shown to include a side arm 70 through which fluids may be injected, even after closure of the through-passage (FIG. 7a). Such a side arm may be provided on the distal portion of the device and include luer threads for connection to a catheter. This embodiment would be particularly useful in contrast injection after a guidewire passing through the closure device is locked into place.

Referring to FIGS. 8 and 8a, another embodiment employing a side arm 80 at a right angle to the through-passage is illustrated, in which a male locking luer 82 is constructed integrally therewith.

Referring to FIGS. 9 and 9a, the closure device 2 is shown for use as a quick hub attachment, by closing the channel 20 upon, for example, an elongated member. The elongated member 90 may be, for example, a small diameter guidewire, as shown, or a tube, and closure device 2 provides a convenient handle for the member as it is torqued during positioning in the body.

With the syringe or any other attachment to the proximal body member of the closure device removed, the device functions as a stop cock (though requiring counter clockwise rotation to close) for controlling flow through a tubing or other such elongated member 90, as shown in FIGS. 9 and 9A, thereby replacing conventional stop cocks and for which no additional drawing is necessary.

Where the automatic opening feature upon connection of a device is not to be employed, threads 13 and 13' may be changed to right hand threads to enable this through-passage stop cock and gripper to close with conventional right hand rotation.

In a very important further embodiment, referring to FIG. 11, a closure device 2a is provided of much larger dimension, (device 2a preferably having an outer diameter of about 1 inch, the tubing having an outer diameter of about 0.316 inch, and the through-passage having an inner diameter of about 0.170 inch) and having the direction of its spiral cam surface and the direction of the threads between the parts of the housing extending in the opposite direction (right handed). This device is connected, e.g. by insert molding, to a thin-walled sheath 120 of between 50 and 150 cm length to provide a catheter introducer sheath assembly, constructed to enable introduction of a placement catheter 124 for the placement of an element, such as a vena cava filter (one type of which is known as a Greenfield filter) into the body. (The closure device and sheath could be joined instead by any other means, e.g. matching luer connectors between the closure device and the sheath). The use of a vena cava filter for filtering out blood clots by its placement in the inferior vena cava is well-known in the medical field. See, e.g. U.S. Pat. No. 3,952,747 to Kimmell, and U.S. Pat. No. 4,817,600 to Herms et al. the texts of which are incorporated herein by reference. The general procedure followed in the embodiment to be illustrated is to use a guidewire (the guidewire may be routed into the desired position using the closure device of FIG. 2 as a gripping means).

Where a guidewire is used, the guidewire is routed through the vasculature in a manner where it can be watched fluoroscopically and manipulated accordingly. Thereafter the thin-walled sheath 120 with attached closure device 2a and containing an elongated flexible dilator 122, with exposed tip 126 (see FIG. 11) is introduced over the guidewire, and once placed, the dilator is withdrawn. Closing the valve of the closure device 2 forms an air-tight and fluid-tight seal around the guidewire, thereby preventing, for example, blood from flowing backwards through the sheath 122. Thus, the guidewire can be temporarily left in place inside the long flexible sheath when used with the closure device of the invention; reliable closure is established around the guidewire by an approximate one-half turn of the proximal body member relative to the distal body member by simple manual rotation of the proximal body portion by grip of the outer cylindrical surface.

Figure 10:
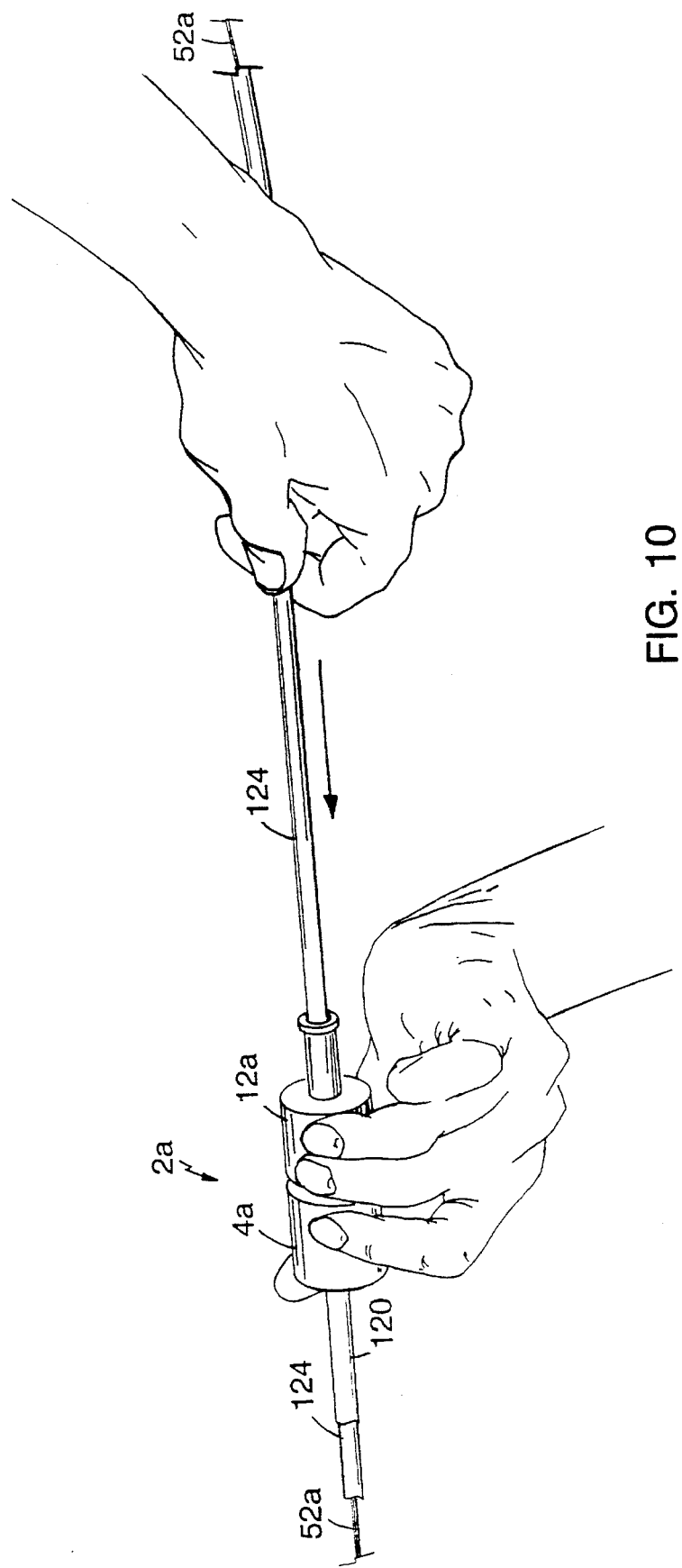
FIG. 10 is a perspective illustration showing combination of a larger closure device according to the invention with an introducer sheath and use of the device as a gripping and closure control device in introducing a catheter, (containing avena cava filter) through the device and sheath, into the vena cava of a patient.
Figure 18:
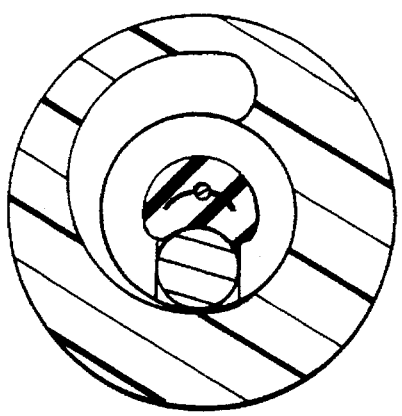
Figure 19:
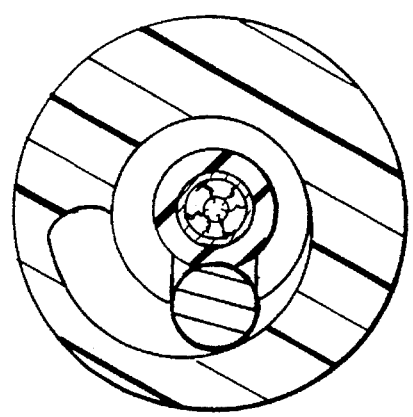
FIG. 19 is a similar view showing the cam in partially closed position in sliding/sealing relation to the filter introducer catheter during insertion of the introducer catheter into the body.
Figure 20:
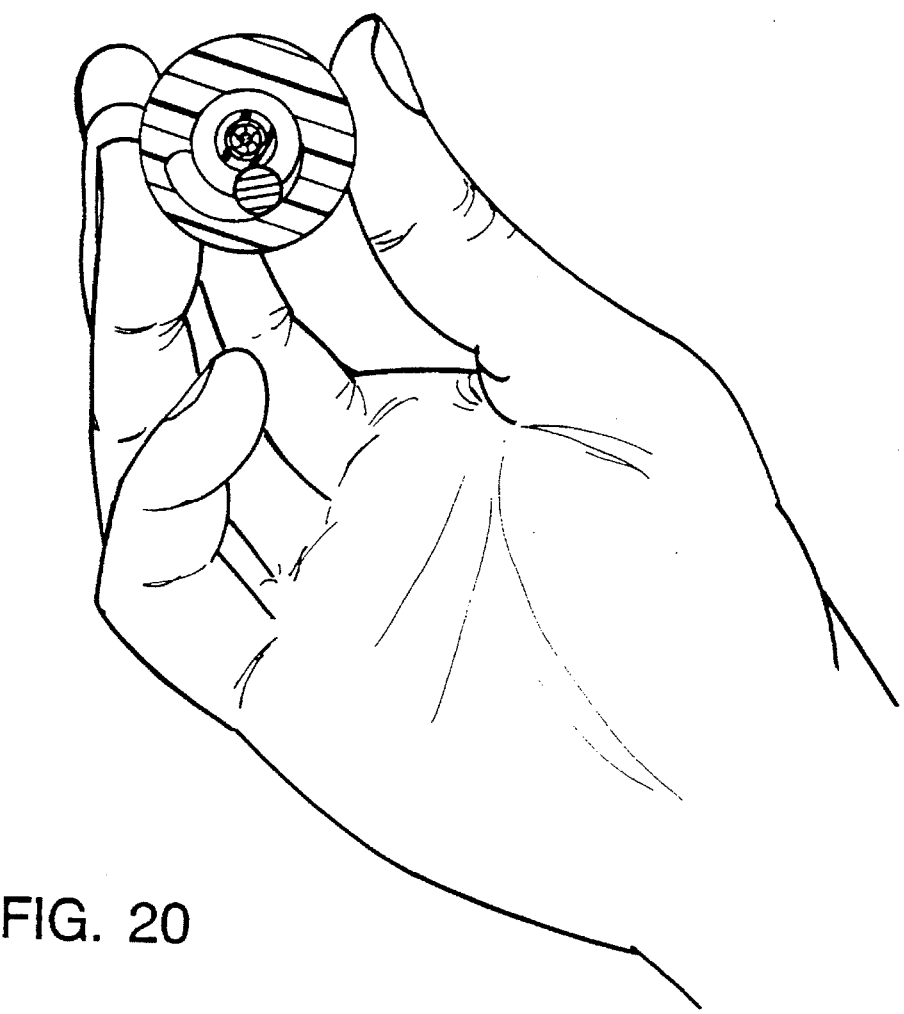
FIG. 20 illustrates relative size of the device in cross-section by depicting it being held by a user who is adjusting the closure by one hand.

The placement catheter 124 containing the vena cava filter 105 is then introduced via the through-passage of the closure device 2a as shown in FIG. 10. For this purpose the proximal portion 12 of the closure device 2a is rotated to open position (in this case, using right hand threads, opening direction is counter clockwise.) After threading of the catheter 122 through the closure device 2a and sheath 120 has begun, as depicted in FIG. 10, the user manipulates the proximal body portion to slightly snug the elastomeric tube against the exterior of the catheter, sufficiently to reduce blood loss along the catheter but insufficient to impede desired sliding of the blood-lubricated catheter into the sheath, see FIG. 17.

The end portion of this catheter which first passes through the closure device is a metal sleeve 103 (FIG. 11a), within which is positioned the vena cava filter 105, characterized in part by its springy legs 107. This is delivered to the vena cava of the patient first by sliding the catheter through the closure device and the sheath and then drawing the sleeve proximally, releasing the filter from the end of the catheter. The use of a metal sleeve as the distal end portion of the catheter enclosing the filter facilitates release of the filter, which has outwardly springable legs, as shown from inside the catheter when the catheter is in position for final placement of the filter in the inferior vena cava.

The filter freely rests in the described metal sleeve of the catheter with a stabilizer 109 within the catheter 122 having a flat surface 111 immediately behind the filter. The stabilizer is connected to a tube 113, a sufficiently axially stiff structure to accomplish the stabilizing effect on the filter. When the catheter is positioned at the desired point in the vessel, the catheter 124 and its distal metal sleeve 103 is pulled proximally, while the stabilizer 109 remains stationary, by means of a reverse action trigger 115 attached to the proximal end of the proximal body member of the closure device. This reverse action operates so that pull-back on the trigger by the operator causes release of the filter from the catheter.

In the catheter placement embodiment of the invention, as mentioned above, the threads by which the proximal portion of the distal body member is connected to the distal portion of the proximal body member are right handed (reversed from the left-handed threading used in the syringe attachment embodiment of the invention). Thus in the catheter placement embodiment, the proximal body member is turned to the left (counter clockwise) relative to the distal body member to open the resilient silicone tubing. This open position is used for introducing the sheath and closure device over the guidewire which passes through the closure device and for introducing the catheter and contained vena cava filter into the sheath. The open (or partially open) position is also maintained during activation of a reverse action trigger at the proximal end of the catheter for deployment of the vena cava filter from the metal sleeve end of the catheter.

As shown in FIG. 12, this embodiment includes side arm 140 through which fluids may be injected after closure of the through-passage by the ball member, after removal of the dilator and prior to insertion of the catheter. This side arm is located on the distal side of the device and includes luer threads for connection to a supply tube that communicates with an elevated source or a to a syringe. This embodiment is useful for flushing the space within the catheter introducer sheath with saline solution containing heparin, to prevent blood clotting which could block the through-passage and obstruct later insertion of the catheter containing the vena cava filter.

Referring to FIGS. 21–21B, 22 and 22A a device is shown which is generally preferred for use in applications in which the valve will be subjected to a wide range of pressures, including high fluid pressure. The device includes a distal body member 202 and a proximal body member assembly 204, each having a gripping surface 206, 206a to facilitate relative rotation by the user. A catheter 205 extends from the distal body member. A window 207 in the distal body member enables the user to view indicia describing the condition of the valve, e.g., "open" and "closed", on the surface of the underlying proximal body-member assembly.

Figure 21:
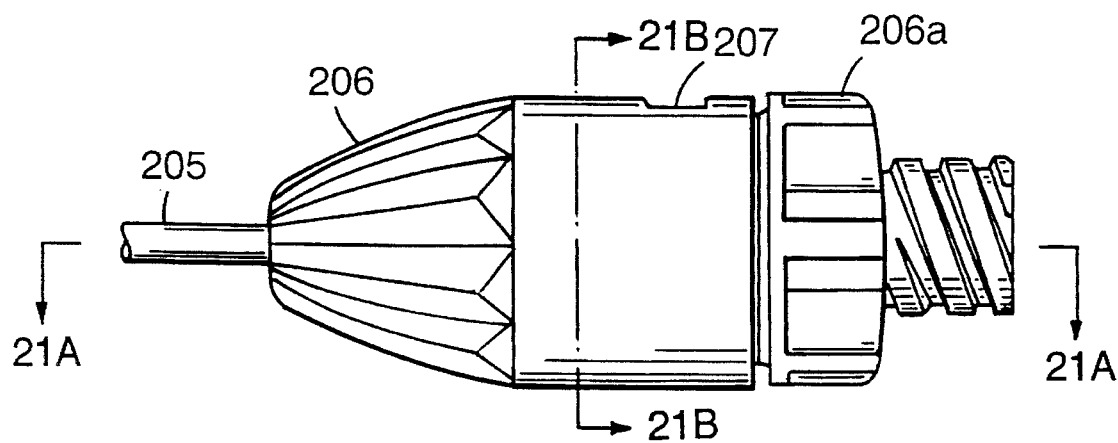
FIG. 21 shows a device according to an alternate preferred embodiment of the invention.
Figure 21A:
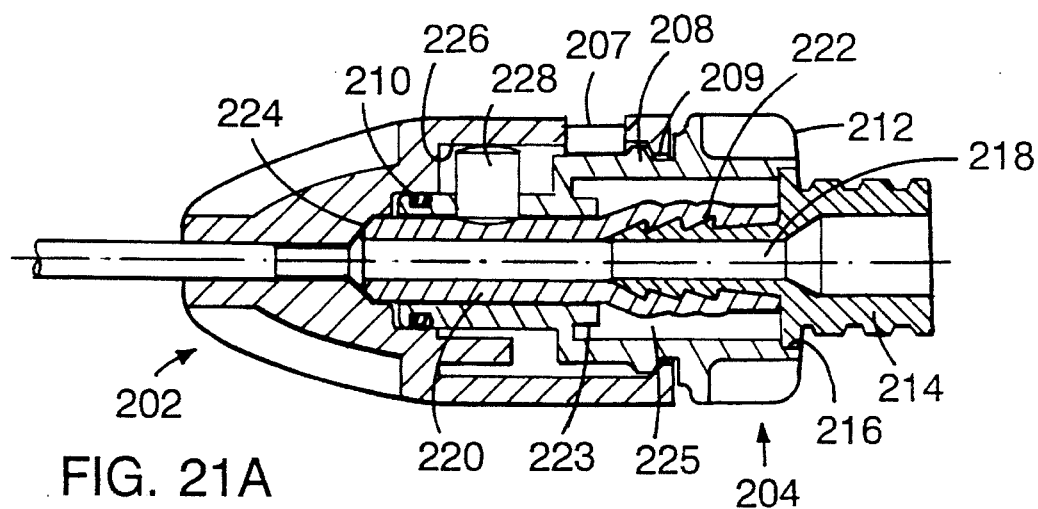
FIGS. 21A and 21B show cross-sectional views of the device of FIG. 21, taken along lines A—A and B—B, respectively.
Figure 21B:
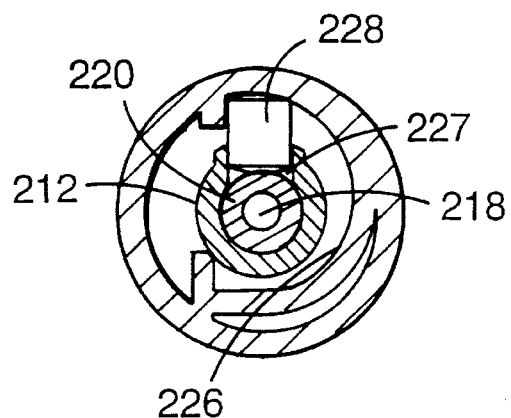

Distal body member 202 securely engages proximal body member assembly 204 by a snap fit engagement of circumferential ridge 208 on proximal body member assembly 204 with shoulder 209 on distal body member 202 (FIG. 21A). A sealing member 210, typically an elastomeric o-ring, disposed near the distal end of the proximal body member, ensures a reliable fluid-tight and air-tight seal between the distal and proximal body members. Should negative pressure be applied to the central lumen (e.g., by drawing back on a syringe connected to the proximal end of the proximal portion), the sealing member 210 provides a primary seal inhibiting air from entering the fluid path when the compression member is in the open position. Under pressurized conditions, the sealing member provides a back-up seal (primary sealing is provided by expansion of tubing member 220). As tubing member 220 will expand less under low pressure conditions, it is under low pressure that the sealing member is most important as a back-up.

Proximal body member assembly 204 includes a first part 212 and a second part 214, which may be pressure fit or bonded together at region 216 (FIG. 21A), e.g., by solvent or ultrasonic bonding. It is preferred, for optimal safety and reliability, that the two parts be bonded together.

A passage 218 extends along the longitudinal axis of the device, and is defined by the inner walls of the proximal and distal body members. A resilient tubing member 220 is disposed within and supported by the passage. The proximal end of the tubing is in sealing engagement with the second part 214, sealed for high pressure by the pressure fit of barbed fitting 222 within the resilient tubing. Sealing is aided by supporting member 223 which limits radial expansion of tubing member 220 and provides a back-up seal of the exterior of the tubing member to the supporting member under pressurized conditions. This back-up seal, in combination with the seal formed at region 216, provides a chamber 225 which will retain any fluid leakage. The distal end of tubing member 220 abuts a tapered surface 224 of distal body member 202.

Distal body member 202 includes an inner circumferential camming surface 226. A radial aperture 227 extends from the outer surface of part 212 to passage 218, and receives and retains a compression member 228. Rotation of distal body member 202 will thus cause the radial position of compression member 228, and thus the compression of the tubing member, to be adjusted, opening and closing the valve.

The material of resilient tubing member 220 is selected to enable it to seal upon itself, when collapsed by compression member 228, or seal upon a medical device such as a catheter or guidewire when present in passage 218.

Referring to FIG. 22, the device is assembled by first assembling proximal body member assembly 204. Barbed fitting 222 is inserted into the proximal end of tubing member 220, and the distal end of tubing member 220 inserted into part 212. Compression member 228 is placed in aperture 227, and sealing member 210 is fitted onto the distal end of part 212. Parts 212 and 214 are bonded together at region 216, forming the proximal body member assembly shown in FIG. 22A. The proximal body member assembly is then snap fit into the distal body member, forming the complete device shown in FIG. 21.

Alternative Embodiments

In conclusion, in its more general aspects the invention can be embodied in many forms too numerous to attempt to mention, as will be understood by the person skilled in the art. As examples only, the distal body member of the closure device could carry an integral, deflectable hinged member in place of the separate spherical compression element as described, as a valve component to be disposed between the cam surface of the proximal body member and the resilient tube to effectuate opening and closing of the tube. Also, although only one cam and associated compression member has been described, in its broader aspect the closure device of the invention is not so limited. For example, two cams could be used with two compression balls, hinged legs, cantilevered elements, or the like on opposing sides, to carry out the tube-opening and closing by means of displacement of the elements in the closure device of the invention by co-rotation of respective cam surfaces. Thus, although a ball-form or sphere has been described as the compression member in the device, the member does not necessarily have to be of that form, nor does it necessarily need to be limited to only one element that bears radially inward on the tubing. Indeed a resilient wall portion of an otherwise rigidly defined passage that can be deflected under the influence of the compression device to close the passage can be employed in place of the resilient tube.

Also, the embodiments described use either right-handed or left-handed threads to Join the distal and proximal body members of the closure device and cause slight axial movement as the compression member moves in opening or closing the tube. The means of joinder and movement between the distal and proximal body members could also be found in other rotatable connections to give the same type of operation, some in which there is no axial advance at all, so the closure device, in certain aspects, is not limited to threaded surfaces for joining the component members.

For the syringe-actuated aspect of the invention, to obtain some of the advantages, it is possible to employ other two-part rotary valve constructions, such as two relatively rotatable disks each having an aperature which through rotation of the disks line up to define the passage and through opposite rotation move out of alignment to close the passage.

It will be understood the foregoing disclosure and description of the invention and alternative constructions are illustrative and explanatory thereof, and various changes in the size, shape and materials, as well as in the details of the illustrated constructions may be made without departing from the spirit of the invention.

We claim:

1. A closure device to which a cooperative component is attachable for communication therebetween, said closure device comprising:

a rotatable body portion including a connector for connection to and disconnection from a mating connector of the cooperative component by relative rotation between said rotatable body portion and the cooperative component, and a relatively stationary body portion of said closure device, said rotatable body portion being rotatable relative to said stationary body portion between an open position in which a passage is defined through said closure device and a closed position in which said passage is closed, said body portions being constructed and arranged such that the direction of relative rotation of said connectors for connection of said rotatable body portion to said cooperative component corresponds to the direction of rotation of said rotatable portion relative to said stationary body portion toward said open position to also open said passage and the direction of relative rotation of said connectors that disconnects said rotatable body portion from said cooperative component corresponds to the direction of rotation of said rotatable body portion relative to said stationary body portion toward said closed position to also close said passage.

2. The closure device of claim 1 further comprising:

a resilient member having an axis at least partially defining said through-passage;

said rotatable body portion including an internal cam having a cam surface oriented about and spaced from the axis of said passage, said cam having a first surface portion disposed relatively closer to said axis than a circumferentially spaced second surface portion, a radially movable compression member disposed between and in such contact with said cam surface and the exterior of said resilient member that said rotation for connecting said component to said closure device causes said cam surface to adjust the radial compression of said resilient member further from said axis to open said passage, and said rotation for disconnecting said component from said closure device causes said cam surface to adjust the radial compression of said resilient member closer to said axis to close said passage.

3. The closure device of claim 2 wherein said resilient member comprises a resilient section of tubing.

4. The closure device of claim 3 wherein said relatively stationary body portion fixes the position of said tubing.

5. The closure device of claim 2 wherein said combination is constructed so that rotational force required to rotate said body portion rotatable to effect change in the compression of said resilient member to open and close said passage is less than the rotational force needed, respectively, to complete the connection and disconnection of said cooperative component relative to said device.

6. The closure device of claim 5 wherein said rotatable body portion is threadably attached about said axis to a said relatively stationary body portion, the threads thereof being opposite to the direction of rotation that enables said device to be rotatably connected to said cooperative component, whereby rotation to connect said cooperative component to said device causes said body portions to move apart.

7. The closure device of claim 6 wherein a stop surface is defined at an end of said second cam surface portion, said stop surface being arranged to engage said compression member and stop relative motion apart of said body portions when said compression member reaches passage-opening position preventing disassembly of said body portion by blocking further rotation and said rotatable and relatively stationary body portions are constructed to engage each other and stop threaded-together motion when said compression member reaches a passage-closing position.

8. The closure device of claim 2 or 5 wherein said closure device is adapted for use as a medical closure device, said passage being dimensioned to pass a pressurized fluid or a medical device into or out of a living body and the proximal end of said device is constructed to be connected to said cooperative catheter or a syringe.

9. The closure device of claim 8 wherein the distal end of said closure device is constructed to be connected to a catheter.

10. The closure device of claim 2 wherein said first surface portion of said cam positions said compression member radially to completely close in fluid-tight manner said through-passage and said second surface portion positions said compression member to fully open said through-passage.

11. The closure device of claim 10 wherein said cam defines a smooth spiral-form surface.

12. The closure device of claim 11 wherein said compression member is a single ball-form member.

13. The device of claim 7 further comprising a screw thread on said rotatable body portion, said screw thread configured to engage a screw thread on said cooperative component, and said cam defines a spiral-form surface with an abrupt transition from the end of said second cam surface portion, furthest from the axis, to a portion of said rotatable body portion closer to the axis in a manner interacting with said compression member, said manner of interacting permitting continual rotation during assembly of said rotatable body portion in a screw-on direction in which the compression member is gradually progressively compressed against said resilient member to the maximum at which state it remains until further rotation causes the second portion of the cam surface to reach said compression member permitting said compression member to spring outwardly to permit continued rotation of said rotatable body portion, whereas opposite rotation of said rotatable body portion along said threads is limited by stopping of said compression member against said abrupt transition of said rotatable body portion.

14. The closure device of claim 7 wherein said compression member is held axially fixed, relative to said resilient member.

15. The closure device of claim 14 wherein said relatively stationary body portion fixes the position of said resilient member and defines a radially extending aperture in which said compression member is axially confined, and permitted to move radially against said resilient member.

16. The closure device of claim 3 wherein said tubing is compressed axially and confined radially for sealing engagement of surfaces at its proximal and distal ends.

17. The closure device of claim 2 wherein said body portions and said passage are sized for passage therethrough of a device and providing, when said closure device is closed upon said device, means for gripping and torquing said device.

18. The closure device of claim 2 wherein said body is attachable at its proximal and distal ends to tubing members for controlling the flow of fluid therethrough.

19. The closure device of claim 2 wherein said rotatable body portion has an external surface exposed for engagement and rotatable operation by the hand of a user.

20. The closure device of claim 2 constructed so that said rotation of said rotatable body portion to open and close said through-passage is substantially one-half turn.

21. The closure device of claim 3 for control of a fluid at a pressure selected from over a wide pressure range wherein the thickness and character of the material of said resilient tubing member is selected to withstand said selected pressure.

22. The closure device of claim 3 for control of a fluid at a flow rate selected from over a wide flow range, wherein the inside diameter of said resilient tubing member is selected to accommodate said selected fluid flow rate.

23. The closure device of claim 1 wherein said body portions, in open position, define a through-passage through which a device can pass.

24. The closure device of claim 1 or 23 wherein the wall defining said passage is constructed to close and seal or grip a device inserted into said through-passage.

25. The closure device of claim 9 wherein said catheter connected to the distal end of said closure device is integrally molded with said closure device.

26. The closure device of claim 8 further including a flexible introducer sheath joined to the distal end of said closure device, and a catheter containing a vena-cava filter and a stabilizer for placement of said filter, said introducer sheath and said closure device defining a passage sized to pass said catheter therethrough, said flexible introducer sheath and said closure device comprising a catheter introducer sheath assembly, and said catheter and said catheter introducer sheath assembly being contained in a catheter introducer kit.

27. The closure device of claim 26 wherein said passage is of the order of ⅛ inch diameter.

28. The closure device of claim 26 wherein said rotatable body portion is threadably attached about said axis to a said relatively stationary body portion and said compression member is adjustable by manual manipulation of said rotatable body portion to selected intermediate rotatable positions relative to said relatively stationary body portion to cause said resilient member to lightly engage the sides of said catheter being inserted through said catheter introducer sheath assembly to impede outward blood flow along the sides of said catheter while permitting slidable insertion thereof.

29. The closure device of claim 26 in combination with a removable elongated dilator disposed in said sheath flexible introducer, said dilator having a tapered distal portion extending distally beyond the sheath flexible introducer.

30. The closure device of claim 29 wherein said dilator has a small axial passage enabling said dilator, sheath flexible introducer and closure device to be slid over a pre-placed guidewire for guiding the sheath into a predetermined position.

31. A medical closure device for providing a passage into or out of the body for both pressurized fluids and a medical device, comprising in combination:

a resilient member at least partially defining said passage, said passage having an axis and sized to pass a selected medical device and pressurized fluid, said resilient member being of material selected, in response to radial pressure applied to said resilient member, to form a pressure seal upon said medical device when said medical device is present in said passage and upon an opposing surface defining said passage when said medical device is not present;

a proximal body portion including first and second members said first member having a pressure fitting in sealing engagement with and mounting said resilient member and said second member disposed about and supporting said resilient member;

a distal body portion including an internal cam having a cam surface oriented about and spaced from the axis of said passage with a first surface portion disposed relatively closer to said axis than a circumferentially spaced second surface portion, and a compression member positioned in a radially extending aperture in said proximal body portion and biased radially outwardly by said resilient member to maintain contact with said cam surface, said proximal and distal body portions being connected together in a manner permitting their relative rotation about said axis, and said body portions and said resilient member being sealed together in a manner to withstand, without leakage, fluid under pressure in said passage;

said connected body portions cooperatively related, whereby, upon relative rotation of said body portions, said cam surface is moved relative to said compression member to cause radial displacement of said compression member closer to the axis of said passage to cause said resilient member to grip and pressure seal upon the exterior of said medical device, when present in said passage, or upon said opposing surface defining said passage when said medical device is not present.

32. The closure device of claim 31 wherein said device further comprises a sealing member mounted on said second part of said proximal body portion to enhance sealing engagement between said distal and said proximal body portions.

33. A method of opening or closing a passage through which both pressurized fluids and a medical device can pass into or out of the body, comprising the steps of:

a) providing a closure device comprising:

a rotatable body portion including a connector for connection to and disconnection from a mating connector of a cooperative component by relative rotation between said rotatable body portion and the cooperative component, and a relatively stationary body portion of said closure device, said rotatable body portion being rotatable relative to said stationary body portion between an open position in which a passage is defined through said closure device and a closed position in which said passage is closed, said body portions being constructed and arranged such that the direction of relative rotation of said connectors for connection of said rotatable body portion to said cooperative component corresponds to the direction of rotation of said rotatable portion relative to said stationary body portion toward said open position to also open said passage and the direction of relative rotation of said connectors that disconnects said rotatable body portion from said cooperative component corresponds to the direction of rotation of said rotatable body portion relative to said stationary body portion toward said closed position to also close said passage, b) connecting or disconnected said cooperative component and said rotatable body portion to open or close said passage, respectively, by relative rotation between said rotatable body portion and the cooperative component.

34. The method of claim 33 further comprising the steps of:

a) introducing a medical device through said passage; and b) while said device is within said passage, causing relative rotation of said second body portion in the direction that disconnects said component from said closure device to cause said resilient member to grip and pressure seal upon the exterior of said device.

35. The method of claim 33 wherein said cooperative component is a syringe for supplying pressurized fluids.

* * * * *

UNITED STATES PATENT AND TRADEMARK OFFICE
CERTIFICATE OF CORRECTION

PATENT NO. : 5,489,274

DATED : February 6, 1996

INVENTOR(S) : Michael S.H. Chu et al.

It is certified that error appears in the above-identified patent and that said Letters Patent is hereby corrected as shown below:

On the cover sheet, the priority data is missing: U.S. Patent Application Serial No. 776,581, filed, 10/11/91.

In the References Cited Section, Other Publications, item [56]:

in the Tuohy-Borst reference, "Medi∝Tech" should be --Medi-Tech--.

in the Quality Check reference, "Burron∝Burron" should be --Burron Burron--.

In the Abstract, line 11, "torqugeable" should be --torquegeable--.

In Col. 2, line 9, "avena" should be --a vena--.

In Col. 6, line 5, "avena" should be --a vena--.

In Col. 7, line 56 "dietally" should be --distally--.

In Col. 10, line 12, "assembly-compression" should be --assembly, compression--.

In Col. 11, line 6, "anglographic" should be --angiographic--.

In Col. 14, line 6, "body-member" should be --body member--.

In Col. 15, line 28, "Join" should be --join--.

UNITED STATES PATENT AND TRADEMARK OFFICE
CERTIFICATE OF CORRECTION

PATENT NO. : 5,489,274

DATED : February 6, 1996

INVENTOR(S) : Michael S.H. Chu et al.

It is certified that error appears in the above-identified patent and that said Letters Patent is hereby corrected as shown below:

In Col 16, claim 2, line 12, "through-passage" should be --passage--.

In Col. 16, claim 5, line 34, after "said" insert --rotatable--.

In Col. 16, claim 5, line 35, after "portion" delete --rotatable--.

In Col. 16, claim 6, line 41, delete "a".

In Col. 18, claim 29, line 31, delete "sheath".

In Col. 18, claim 29, line 32, after "introducer" insert --sheath--.

In Col. 18, claim 29, line 33, delete "sheath".

In Col. 18, claim 29, line 33, after "introducer" insert --sheath--.

In Col. 18, claim 30, line 35, delete "sheath".

UNITED STATES PATENT AND TRADEMARK OFFICE
CERTIFICATE OF CORRECTION

PATENT NO. : 5,489,274
DATED : February 6, 1996
INVENTOR(S) : Michael S.H. Chu et al.

It is certified that error appears in the above-indentified patent and that said Letters Patent is hereby corrected as shown below:

In Col. 18, claim 30, line 36, after "introducer" insert --sheath--.

Signed and Sealed this

Twenty-sixth Day of November 1996

BRUCE LEHMAN

Attest:

Attesting Officer

Commissioner of Patents and Trademarks